(12) United States Patent
Hickey et al.

(10) Patent No.: US 8,383,615 B2
(45) Date of Patent: Feb. 26, 2013

(54) AZETIDINE 2-CARBOXAMIDE DERIVATIVES WHICH MODULATE THE CB2 RECEPTOR

(75) Inventors: Eugene Richard Hickey, Danbury, CT (US); Doris Riether, Biberach an der Riss (DE); David Smith Thomson, Ridgefield, CT (US); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/376,203

(22) PCT Filed: Jun. 8, 2010

(86) PCT No.: PCT/US2010/037696
§ 371 (c)(1),
(2), (4) Date: Jan. 10, 2012

(87) PCT Pub. No.: WO2010/147791
PCT Pub. Date: Dec. 23, 2010

(65) Prior Publication Data
US 2012/0142666 A1  Jun. 7, 2012

Related U.S. Application Data

(60) Provisional application No. 61/187,394, filed on Jun. 16, 2009.

(51) Int. Cl.
*A61K 31/397* (2006.01)
*C07D 413/14* (2006.01)
*C07D 417/14* (2006.01)
*C07D 405/04* (2006.01)

(52) U.S. Cl. .............. 514/210.18; 548/953; 546/272.1; 544/58.2

(58) Field of Classification Search .............. 514/210.18; 548/953, 233, 128, 195, 163, 214, 245; 546/272.1; 544/58.2
See application file for complete search history.

(56) References Cited

U.S. PATENT DOCUMENTS

| 3,116,284 | A | 12/1963 | Testa |
| 3,117,128 | A | 1/1964 | Mooradian |
| 3,577,462 | A | 5/1971 | Bruce et al. |
| 3,966,809 | A | 6/1976 | Baker et al. |
| 4,257,954 | A | 3/1981 | Schmidt et al. |
| 4,535,087 | A | 8/1985 | Spatz |
| 4,672,065 | A | 6/1987 | Spatz |
| 4,734,125 | A | 3/1988 | Gehring et al. |
| 4,859,707 | A | 8/1989 | Loftsson et al. |
| 5,256,658 | A | 10/1993 | Hsi et al. |
| 5,428,037 | A | 6/1995 | Pascal et al. |
| 5,475,130 | A | 12/1995 | Sato et al. |
| 5,571,921 | A | 11/1996 | Bender et al. |
| 5,583,147 | A | 12/1996 | Ko et al. |
| 5,656,634 | A | 8/1997 | Chang et al. |
| 5,847,153 | A | 12/1998 | Warpehoski et al. |
| 5,958,940 | A | 9/1999 | Rane et al. |
| 5,968,929 | A | 10/1999 | Blythin et al. |
| 6,057,371 | A | 5/2000 | Glennon |
| 6,176,442 | B1 | 1/2001 | Eicher et al. |
| 6,221,866 | B1 | 4/2001 | Brendel et al. |
| 6,355,653 | B1 | 3/2002 | Trottmann et al. |

(Continued)

FOREIGN PATENT DOCUMENTS

| CH | 312963 A | 3/1956 |
| DE | 1080563 B | 12/1957 |
| EP | 0628555 | 12/1994 |
| EP | 0929519 | 7/1999 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |
| GB | 884258 A | 12/1961 |

(Continued)

OTHER PUBLICATIONS

Sheehan et al., The Synthesis and Reactions of Some Substituted Beta-Lactams, 1951, Journal of the American Chemical Society, 73, 1761-1765.*

(Continued)

*Primary Examiner* — Kristin Bianchi
(74) *Attorney, Agent, or Firm* — Michael P. Morris; Anthony P. Bottino

(57) ABSTRACT

Compounds of the formula (I), (II) and (III) which modulate the CB2 receptor are disclosed. Compounds according to the invention bind to and are agonists of the CB2 receptor, and are useful for treating inflammation. Those compounds which are agonists are additionally useful for treating pain.

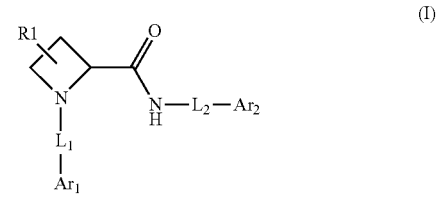

(I)

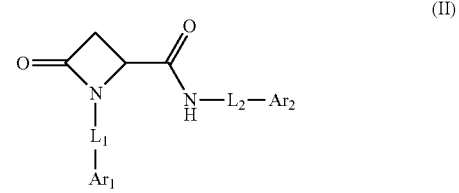

(II)

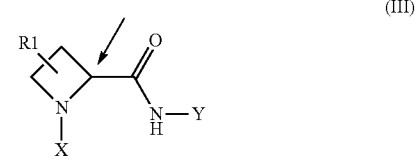

(III)

17 Claims, No Drawings

U.S. PATENT DOCUMENTS

| | | |
|---|---|---|
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,776,897 B2 | 8/2010 | Murakami et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 2002/0099035 A1 | 7/2002 | Sandanayaka et al. |
| 2004/0067999 A1 | 4/2004 | Block et al. |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2006/0061726 A1 | 3/2006 | Okuyama |
| 2006/0079557 A1 | 4/2006 | Dolle et al. |
| 2007/0021403 A1 | 1/2007 | Abouabdellah et al. |
| 2007/0021430 A1 | 1/2007 | Chen et al. |
| 2007/0093501 A1 | 4/2007 | Kubo et al. |
| 2007/0179126 A1 | 8/2007 | Casellas et al. |
| 2007/0191340 A1 | 8/2007 | Zindell et al. |
| 2007/0213311 A1 | 9/2007 | Li et al. |
| 2008/0039464 A1 | 2/2008 | Berry et al. |
| 2008/0064690 A1 | 3/2008 | Atkinson et al. |
| 2008/0081342 A1 | 4/2008 | Fung |
| 2008/0081822 A1 | 4/2008 | Berry et al. |
| 2009/0163545 A1 | 6/2009 | Goldfarb |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |

FOREIGN PATENT DOCUMENTS

| | | |
|---|---|---|
| GB | 1237126 A | 6/1971 |
| JP | 61027905 U | 2/1986 |
| JP | 61027955 A | 2/1986 |
| JP | 61126071 A | 6/1986 |
| JP | 2003155285 | 5/2003 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9811097 A1 | 3/1998 |
| WO | 9813340 | 4/1998 |
| WO | 9838163 A1 | 9/1998 |
| WO | 0008015 A2 | 2/2000 |
| WO | 0100573 | 1/2001 |
| WO | 0129007 | 4/2001 |
| WO | 0164651 | 9/2001 |
| WO | 02051806 | 7/2002 |
| WO | 02088089 A1 | 7/2002 |
| WO | 02062750 | 8/2002 |
| WO | 03037274 A2 | 5/2003 |
| WO | 03055482 | 7/2003 |
| WO | 04000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004026301 A1 | 4/2004 |
| WO | 2004029027 | 4/2004 |
| WO | 2004042351 A2 | 5/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006030805 A1 | 3/2006 |
| WO | 2006060461 | 6/2006 |
| WO | 2006074445 A2 | 7/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 A2 | 6/2007 |
| WO | 2007080382 A1 | 7/2007 |
| WO | 2007102059 | 9/2007 |
| WO | 2007118041 A1 | 10/2007 |
| WO | 2007140385 A2 | 12/2007 |
| WO | 2008014199 A2 | 1/2008 |
| WO | 2008023159 A1 | 2/2008 |
| WO | 2008039645 A1 | 4/2008 |
| WO | 2008048914 A1 | 4/2008 |
| WO | 2008064054 A2 | 5/2008 |
| WO | 2008098025 A1 | 8/2008 |
| WO | 2008104994 A2 | 9/2008 |
| WO | 2009055357 A1 | 4/2009 |
| WO | 2009061652 A1 | 5/2009 |
| WO | 2009077533 A1 | 6/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |
| WO | 2011088015 A1 | 7/2011 |
| WO | 2011109324 A1 | 9/2011 |
| WO | 2012012307 A1 | 1/2012 |

OTHER PUBLICATIONS

Gartst, M., et al., "Hydroformylation of bisolefinic amine derivatives catalyzed by cobalt and rhodium". Journal of Organic Chemistry, vol. 46, 1981, pp. 4433-4438.

Gavalda, et al N-Sulfonyl hydroxamate derivataties as inhibitors of class II fructose-1, 6-diphosphate aldolase, Bioorganic & Medicinal Chemistry Letter, 2005, vol. 15, No. 24, pp. 5375-5377.

Goldschmidt,ST. et al., "Biphenyl derivatives II. Basic 4-Biphenyl Compounds". Receuil Travaux Chimiques Des Pays-Bas, vol. 69, 1950, pp. 1109-1117.

Grothe, V. W. et al. "Effect of Potassium Sulfhydrate etc. on Chloroacetylanilides". Archiv der Pharmazie (Weinheim), vol. 238, 1980, p. 600-614.

Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60.

Hanus, L. et al., "HU-308: A specific agonist for CB2, a peripheral cannabinoid receptor", PNAS, 1999, vol. 96, No. 25, p. 14228.

Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.

Huang, X. et al., "A Novel Synthesis of Sulfones via the O,O-Diethylphosphorotellurite Ion-assisted Coupling of Arenesulfonyl Chlorides with Active Halides". Synthetic Communications, 20(15), 2291-2291-2295 (1990).

Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.

Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.

Iddon, B. et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.

Igarashi, J. et al., "Improved synthesis of quinine alkaloids with the Teoc protective group". Tetrahedron letters, Elsevier, Amsterdam, vol. 46, No. 37, 2005, pp. 6381-6384.

Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).

Johansen et al., AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.

Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.

Katz, L., et al., "Hydrazine Derivatives. II. Ortho-Mercapto-Pyridinecarbohydrazides", Contribution from Schenley Laboratories, Inc., 1953, p. 711.

Klein, T. W., et al., "The Cannabinoid system and immune modulation", J. Leukocyte Biology, 2003, vol. 74, p. 486.

Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

Krutosikova, A. et al., "Furan derivatives. LV. Preparation of 5-aryl-2-furfuryl phenyl and 5-aryl-2-furfuryl 4-toly1 sulfones". Chemick Zvesti—Chemical Papers, Veda Bratislava, SK. vol. 28, Jan. 1, 1974, pp. 414-417, ISSN: 0366-6352, p. 414, compounds I-IX.

Lambeng, N. et al., "Discovery of a Novel Piperidinyl-Sulfonyl Benzoic Ester, Active as CB1 Agonist" POSTER. 231st ACS National Meeting, Atlanta, GA. Mar. 26-30, 2006.

Lesser, R. et al. "Homo-?-oxythionaphthene (4-Ketoisothiochromane". Charlottenburg, Industrial Chemistry Laboratory of the Institute of Technology, 1923, pp. 1642-1648.

Lutz, R. E. et al., "Antimalarials. Some piperazine derivatives". Journal of Organic Chemistry, vol. 12, 1947, pp. 771-775.

Mahmoud, A. M. et al., "Synthesis and Biological Activity of Some new 2-(N-Substituted Carboxamidomethyl Thio)-Naphth[1,2-d]Oxazoles—Part V". XP002068972, J. Indian Chem. Soc., vol. LIX, May 1982, pp. 675-677.

Malan Jr., T. P., et al., "CB2 cannabinoid receptor-mediated peripheral antinociception", PAIN, 2001, vol. 93, p. 239.

Markley, L. D., et al., "Antipicornavirus activity of substituted Phenoxybenzenes and Phenoxypyridines", J. Med. Chem., 1986, vol. 29, p. 427.

Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35. In press, accepted manuscript.

Messinger, P., "Sulfones via Mannich bases" Archiv der Pharmazie, 1973, vol. 306, No. 8, pp. 603-610, ISSN: 0365-6233. p. 607, compounds 28A-29C.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Office Action from the EPO for 09-0388 dated Mar. 22, 2010.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp. 5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.

Seidel M. C. et al., "Reaction of Substituted 2-carbethoxyacetyl-aminopyridines and similar compounds with triethyl orthoformate and zinc chloride". Rohm and Haas Company, Spring House, Pennsylvania 19477, 1989.

Sharkey, K. A. et al., "CB2 cannabinoid receptors: new vistas", The first International Conference devoted to studies of the CB2 cannabinoid receptor. Banff, Alberta, Canada, May 31-Jun. 3, 2007.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Smith, S. R., et al., "The anti-inflammatory activities of cannabinoid receptor ligands in mouse peritonitis models", Eur. J. Pharmacology, 2001, vol. 432, p. 107.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Swanson, D. M. et al., "Identification and biological evaluation of 4-*(3-trifluoromethylpyridin-2-yl)piperzine-1-carboxylic acid (5-trifluoromethylpyridin-2-yl)amide, a high affinity TRPV1 (VR1) vanilloid receptor antagonist". Journal Med. Chem, 2005, 48, pp. 1857-1872.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Ueber sulfonirte buttersauren", J. Prakt. Chem., 1899, 1991, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Venkov, A.P. et al., "A new synthesis of 1,2,3,40tetrahydro-2-methyl-4-phenylisoquinolines". Dept of Chemistry, University of Plovdiv, Bulgaria, pp. 253-255, Mar. 1990.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al., "An enantioselective synthesis of sulphonamide hydroxamic acids as matrix metalloproteinase inhibitors", Pergamon, Tetrahedron Letters 43 (2002) 683-685.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

Zindell, R. et al., "Discovery of a novel class of CB2 agonists". General Poster Session. The 235th ACS National Meeting, New Orleans, LA, USA. Apr. 6-10, 2008.

Kano, S. et al., "Formation of Some Heterocycles through Ring Transformation of 1-Arylaxetidin-2-Ones." Heterocycles, vol. 8, No. 1, Dec. 30, 1977, p. 411-416.

International Search Report and Written Opinion for PCT/US2010/037696 mailed Sep. 13, 2010.

Abstract in English for JP 61-027905, Feb. 7, 1986, and WO199626925, Sep. 1996, Derwent Abstract.

Abstract in English for JP 61-027955, Feb. 7, 1986, Derwent.

Abstract in English for JP2003155285, May 27, 2003, Inventor: T. Makoto.

Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.

Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.

Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.

Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.

Arevalo-Martin, A. et al., "Therapeutic Action of Cannabinoids in a Murine model of Multiple Sclerosis", J. of Neuroscience, 2003, vol. 23, No. 7, p. 2511.

Atwell, G. J. et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.

Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.

Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.

Baker, D. et al., "Cannabinoids control spasticity and tremor in a multiple sclerosis model", Nature, 2000, vol. 404, p. 84.

Baltzly, R. et al., "The preparation of N-mono-substituted and unsymmetrically disubstituted piperzines". Journal of American Chemical Society, vol. 66, 1944, pp. 263-265.

Baltzly,R. et al., "Unsymmetrically substituted piperazines. V. Piperazine ureas". The Journal of the American Chemical Society, vol. 76, 1954, pp. 1165-1166.

Balzarini, J. et al., "Antiretroviral activity of semisynthetic derivatives of glycopeptide antibiotics". J. Med. Chem., 2003, vol. 46, No. 13, pp. 2755-2764.

Beilstein Database—Beilstein Registry No. 1084348. CAS Registry No. 6125-28-8. Beilstein Institute for Organic Chemistry. 1966, Abstract.

Beilstein Database—Beilstein Registry No. 1179643. CAS Registry No. 54890-73-2. Beilstein Institute for Organic Chemistry. 1974, Abstract.

Beilstein Database—Beilstein Registry No. 5396840. CAS Registry No. 54890-82-3. Beilstein Institute for Organic Chemistry. 1974, Abstract.

Beilstein Database—Beilstein Registry No. 5398283. CAS Registry No. 68558-02-01. Beilstein Institute for Organic Chemistry. 1978, Abstract.

Beilstein Database—Beilstein Registry No. 857451. CAS Registry No. 37901-58-9. Beilstein Institute for Organic Chemistry. 1972, Abstract.

Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, vol. 36, p. 809.

Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.

Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.

Buckley, N. E. et al., "Immunomodulation by cannabinoids is absent in mice deficient for the cannabinoid CB2 receptor", Eur. J. Pharmacology, 2000, vol. 396, p. 141.

Caplus—1990:497413, Zara-Kaczian, Acta Chimica Hungarica, 1989.

Caplus—RN 112298-90-5 (Tommasi), retrieved from CAPLUS on Jan. 2, 2009.

Caplus—RN 262371-16-4 (Organ), retrieved from CAPLUS on Jan. 2, 2009.

Caplus—RN 57992-82-2 (Babayan), retrieved from CAPLUS on Jan. 2, 2009.

Carenzi, A, et al., "New Isoxazole Derivatives Provided with Antihypertensive Activity". Arzneimittel-Forschung, vol. 39, No. 6, 1989, p. 624-646.

Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.

Chang, M. Y. et al, "Reaction of different a-sulfonyl acetamides with methyl acrylate". Tetrahedron 58 (2002) p. 5075-5080.

Chem Abstract—Accession No. 126:89390, Abstract of JP8311026, Kumaiai Chemical Industry Co., Nov. 26, 1996.

ChemAbstract: 246020-62-2 registry copyright ACS on STN, entered 1999. CHEMCATS.

ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.

ChemAbstracts: 693218-49-4 and 402562-90-7. 2004.

Chen, D. et al., "Preparation, properties, and synthetic potentials of novel boronates in a flourous version (flourous boronates)". Organic Letters, vol. 4. No. 6, 2002, pp. 1003-1005.

Clark, N. G. et al., "The Fungicidal Activity of Substituted Acetanilides and Related Compounds". Biochemical Journal, 1953, vol. 55, p. 839-851.

Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.

Dav, Jr., R. A. et al., "Polarography of phenyl 2-thienyl and 2,2'-dithienyl ketones". 1953.

El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.

EP Office Action for Case 09-0388 dated Mar. 22, 2010.

Ermann, M. et al., "Arylsulfonamide CB2 receptor agonists: SAR and optimization of CB2 selectivity", Bioorganic and Medicinal Chemistry Letters 18 (2008) 1725-1729.

Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.

Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.

Evans, W. J. et al., "A Rearrangement of Carbamyl-sulphones and -sulphides". Journal of the Chemical Society, 1936, p. 329-331.

Faucher, A. M. et al., "Discovery of Small-Molecule Inhibitors of the ATPase Activity of Human Papillomavirus E1 Helicase", J. Med. Chem., 2004, vol. 47, p. 18.

Field, L. et al., "Grignard Reagents of Sulfones. IV. Reactions with Nitriles, Esters and an Isocyanate". Journal of American Society, vol. 78, 1956, p. 4389-4394.

Field, L., et al., "Methyl p-Tolyl Sulfone", Organic Syntheses, Coll. vol. 4, p. 674, 1963; vol. 38, p. 62, (1958).

Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.

Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.

* cited by examiner

AZETIDINE 2-CARBOXAMIDE DERIVATIVES WHICH MODULATE THE CB2 RECEPTOR

APPLICATION DATA

This application claims benefit to U.S. provisional application Ser. No. 61/187,394 filed Jun. 16, 2009.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of *cannabis* is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of *cannabis*.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of *cannabis*, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:.486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various inflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87.Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In one generic aspect of the invention there is provided a compound of the formula (I)

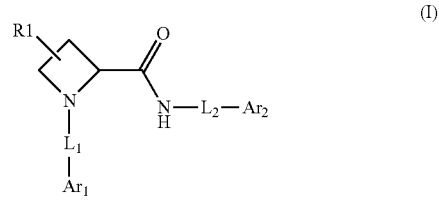

(I)

wherein:

$Ar_1$ is chosen from $C_{1-5}$ alkyl, carbocycle, heterocyclyl and heteroaryl each optionally substituted by 1-3 $C_{1-5}$ alkyl which is optionally substituted with halogens, $C_{1-5}$ alkoxy, hydroxyl, CN, halogen, $NO_2$, —S(O)$_m$—$C_{1-5}$ alkyl, —$CO_2$—$C_{1-5}$ alkyl, —NH($C_{1-5}$ alkyl)-$CO_2$—$C_{1-10}$ alkyl, —C(O)—NH($C_{1-5}$ alkyl), —C(O)—N($C_{1-5}$ alkyl)$_2$, —NH (C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl, carbocycle and heterocyclyl;

Ar$_2$ is chosen from carbocycle, heterocyclyl and heteroaryl each optionally substituted by 1-3 C$_{1-10}$ alkyl which is optionally substituted with halogens, C$_{3-10}$ cycloalkyl, carbocycle, C$_{1-10}$ alkylcarbocycle, heteroaryl, CN or halogen, wherein the C$_{1-10}$ alkyl and carbocycle may be additionally optionally substituted by halogen, hydroxyl or C$_{1-5}$ alkoxy;

L$_1$ is chosen from a bond or C$_{1-5}$ alkyl chain wherein each —CH$_2$— of said chain is optionally replaced by C(O), or S(O)$_m$;

L$_2$ is chosen from a bond or C$_{1-5}$ alkyl chain;

R$_1$ is chosen from hydrogen, oxo (=O) and OH;

m is 0, 1 or 2;

or a pharmaceutically acceptable salt thereof.

The compound according to the embodiment described immediately above and wherein:

Ar$_1$ is chosen from C$_{1-5}$ alkyl, phenyl, C$_{3-6}$ cycloalkyl, dioxanyl, tetrahydrofuranyl, tetrahydropyranyl, thiomorpholinyl, 1,1-Dioxo-1λ$^6$-thiomorpholinyl, morpholinyl and pyridinyl, each optionally substituted by 1-3 C$_{1-5}$ alkyl which is optionally substituted with halogens, C$_{1-5}$ alkoxy, hydroxyl, CN, S(O)$_m$—C$_{1-3}$ alkyl or halogen, Ar$_2$ is chosen from oxazolyl, isoxazolyl, oxadiazoyl, thiazoyl, thiadiazoyl, benzothiazoyl, triazoyl, isothiazoyl, phenyl, pyrimidinyl, pyridizinyl, pyrazinyl and pyridinyl, each optionally substituted by 1-3 C$_{1-6}$ alkyl which is optionally substituted with halogens, C$_{1-5}$ alkoxyl, or hydroxyl, phenyl optionally substituted with halogens, halogen or C$_{3-8}$ cycloalkyl;

R$_1$ is hydrogen;

L$_1$ is a bond, or C$_{1-3}$ alkyl chain wherein each —CH$_2$— of said chain is optionally replaced by C(O) or S(O)$_m$;

L$_2$ is a bond

The compound according to the embodiment described immediately above and wherein:

Ar$_1$ is chosen from C$_{1-5}$ alkyl, phenyl, C$_{3-6}$ cycloalkyl, tetrahydropyranyl and pyridinyl, each optionally substituted by 1-3 C$_{1-5}$ alkyl, trifluoromethyl, S(O)$_m$—C$_{1-3}$ alkyl or halogen;

Ar$_2$ is chosen from isoxazolyl, oxazolyl, thiazolyl, phenyl, benzothiazolyl, isothiazolyl and thiadiazolyl, each optionally substituted by 1-3 C$_{1-5}$ alkyl optionally substituted with C$_{1-5}$ alkoxyl, or hydroxyl, phenyl optionally substituted with halogen, halogen, C$_{3-6}$ cycloalkyl or trifluoromethyl;

L$_1$ is a bond, —CH$_2$—, C(O) or S(O)$_2$;

The compound according to the embodiment described immediately above and wherein:

Ar$_1$ is chosen from C$_{3-5}$ alkyl, phenyl, cyclopentyl, cyclohexyl, tetrahydropyranyl and pyridinyl, each optionally substituted by 1-3 C$_{1-3}$ alkyl, trifluoromethyl, methylsufonyl or halogen;

The compound according to the embodiment described immediately above and wherein:

Ar$_2$ is chosen from

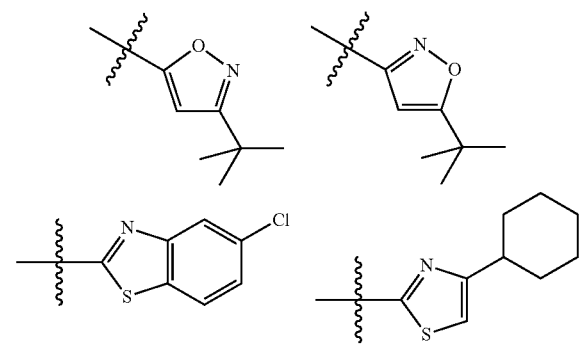

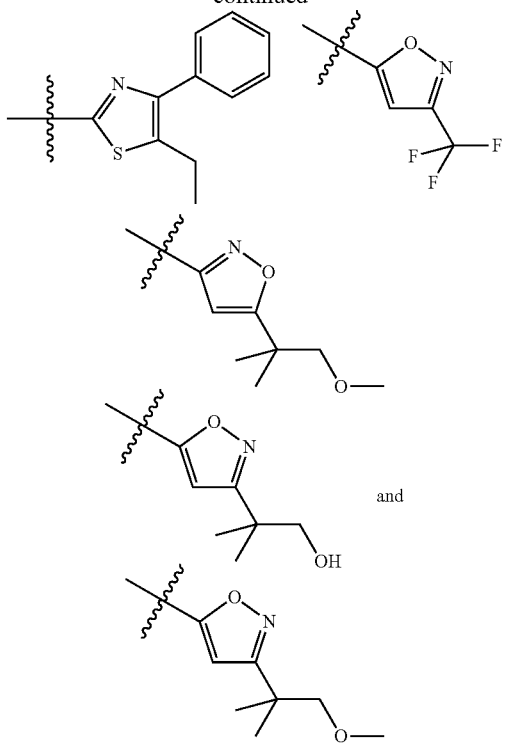

and

The compound according to the embodiment described immediately above and wherein:

Ar$_2$ is chosen from

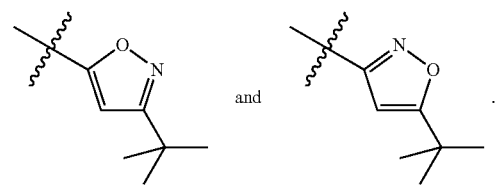

.

In another generic aspect of the invention there is provided a compound of the formula (II)

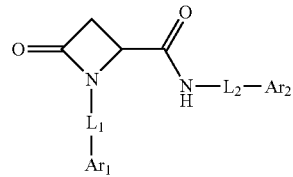

(II)

wherein

Ar$_1$ is chosen from C$_{1-5}$ alkyl, phenyl, C$_{3-6}$ cycloalkyl, dioxanyl, tetrahydrofuranyl, tetrahydropyranyl, oxazolyl, isoxazolyl, oxadiazoyl, thiazoyl, thiadiazoyl, benzothiazoyl, triazoyl, isothiazoyl, pyridinyl, pyrimidinyl, pyrazinyl, pyridazinyl, pyrrolyl, imidazolyl and pyrazolyl each optionally substituted by 1-3 C$_{1-6}$ alkyl which is optionally substituted with halogens, S(O)$_m$—C$_{1-3}$ alkyl, C$_{1-6}$ alkoxy, hydroxyl or halogen, Ar$_2$ is chosen from oxazolyl, isoxazolyl, oxadiazoyl, thiazoyl, thiadiazoyl, benzothiazoyl, triazoyl, isothiazoyl, phenyl, pyrimidinyl, pyridizinyl, pyrazinyl and pyridinyl, each optionally substituted by 1-3 C$_{1-6}$ alkyl which is optionally substituted with halogens, C$_{1-6}$ alkoxyl or hydroxyl, phenyl optionally substituted with halogens, halogen, C$_{1-6}$ alkoxyl, or C$_{3-8}$ cycloalkyl;

L$_1$ is a bond or C$_{1-3}$ alkyl chain;

L$_2$ is a bond;

The compound according to the embodiment described immediately above and wherein:

Ar$_1$ is chosen from C$_{1-5}$ alkyl, phenyl, C$_{3-6}$ cycloalkyl, tetrahydropyranyl and pyridinyl, each optionally substituted by 1-3 C$_{1-6}$ alkyl, trifluoromethyl, S(O)$_m$—C$_{1-3}$ alkyl or halogen;

Ar$_2$ is chosen from isoxazolyl, oxazolyl, thiazolyl, phenyl, benzothiazolyl, isothiazolyl and thiadiazolyl, each optionally substituted by 1-3 C$_{1-6}$ alkyl optionally substituted with C$_{1-6}$ alkoxyl or hydroxyl, phenyl optionally substituted with halogen, halogen, C$_{1-6}$ alkoxyl, C$_{3-6}$ cycloalkyl or trifluoromethyl;

L$_1$ is a bond, or —CH$_2$—;

The compound according to the embodiment described immediately above and wherein:

Ar$_1$ is chosen from C$_{3-5}$ alkyl, phenyl, cyclopentyl, cyclohexyl, tetrahydropyranyl and pyridinyl, each optionally substituted by 1-3 C$_{1-3}$ alkyl, trifluoromethyl or halogen;

The compound according to the embodiment described immediately above and wherein:

Ar$_2$ is chosen from

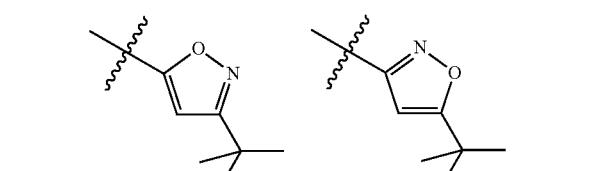

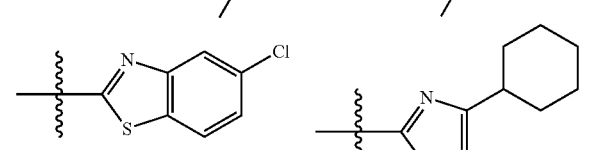

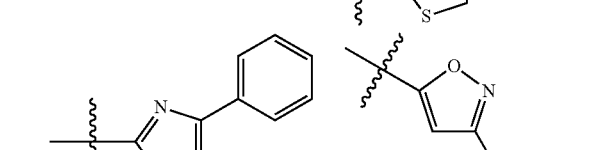

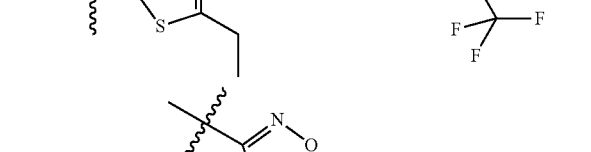

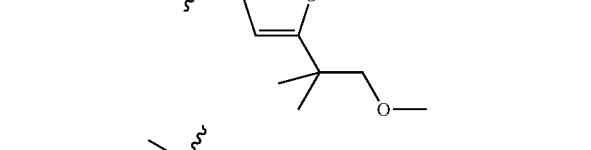

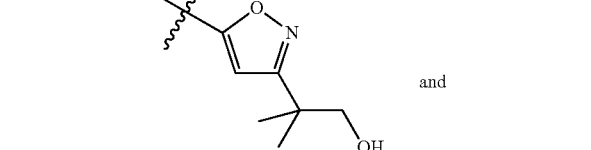

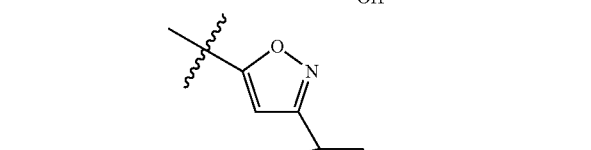

The compound according to the embodiment described immediately above and wherein:

Ar$_2$ is chosen from

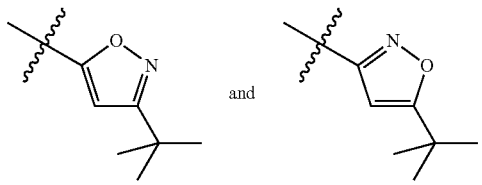

and

In another generic aspect of the invention there is provided a compound of the formula (III)

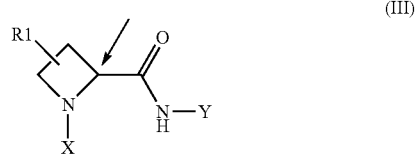

(III)

wherein

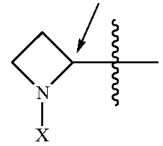

of the formula (III) is chosen from A1-A15 of Table I, and

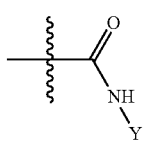

of the formula (III) is chosen from B1-B25 of Table I,

TABLE I

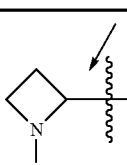

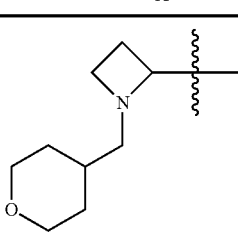

A1

TABLE I-continued
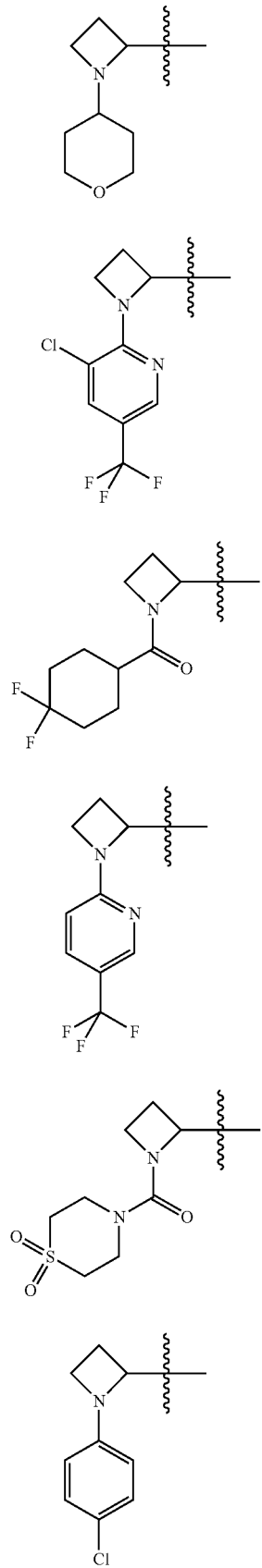
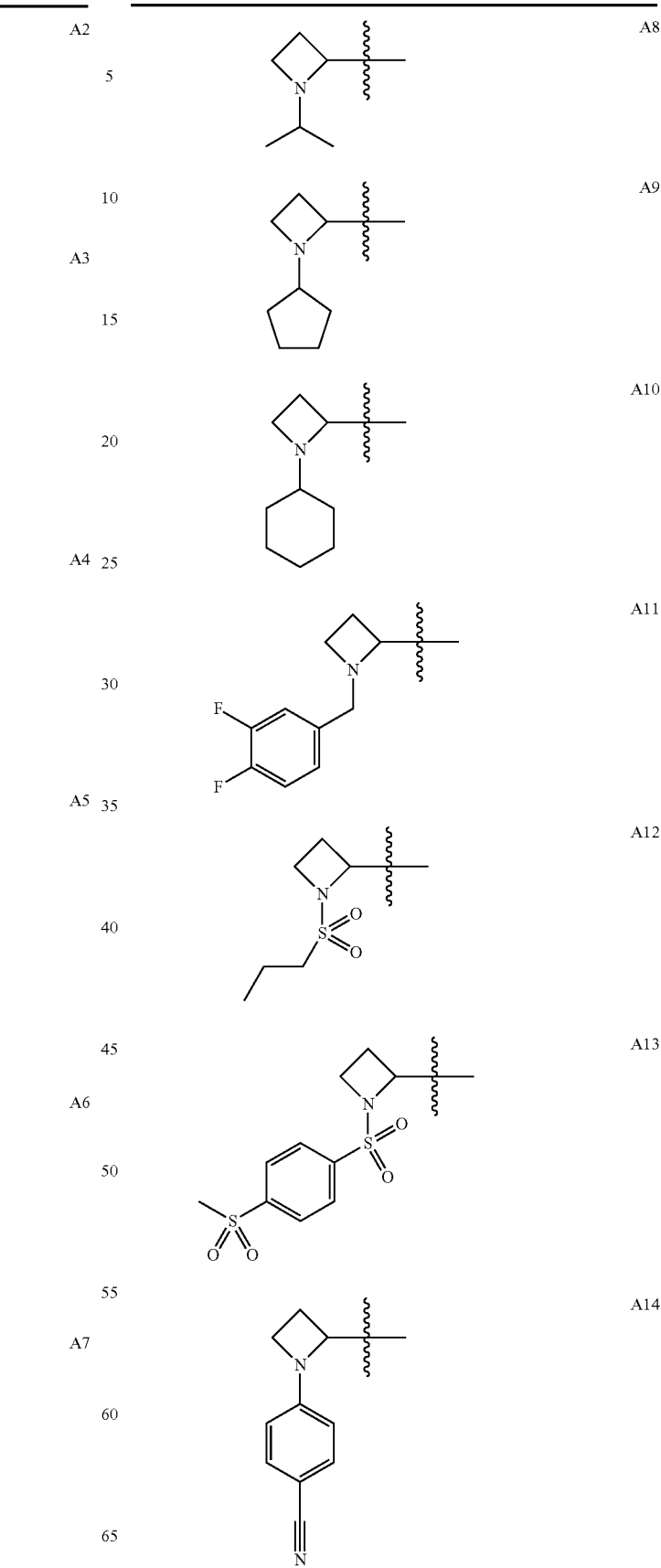

TABLE I-continued
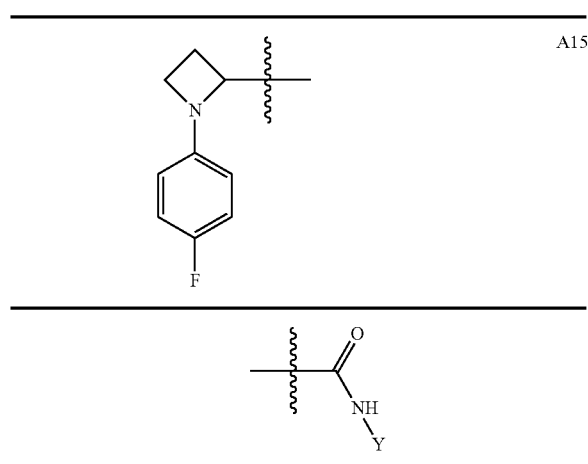
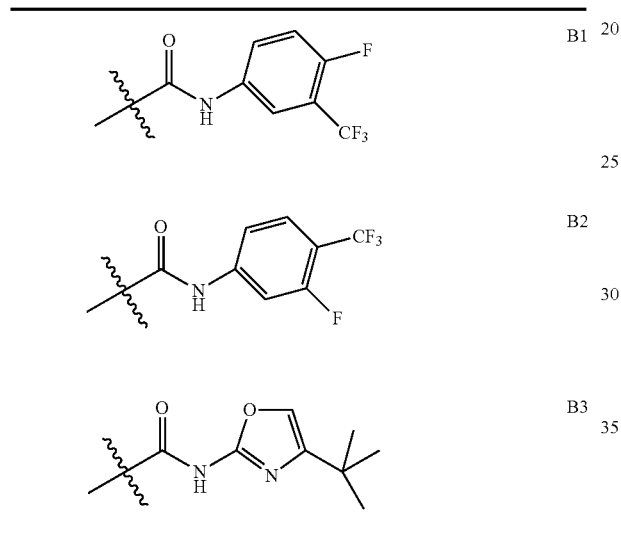
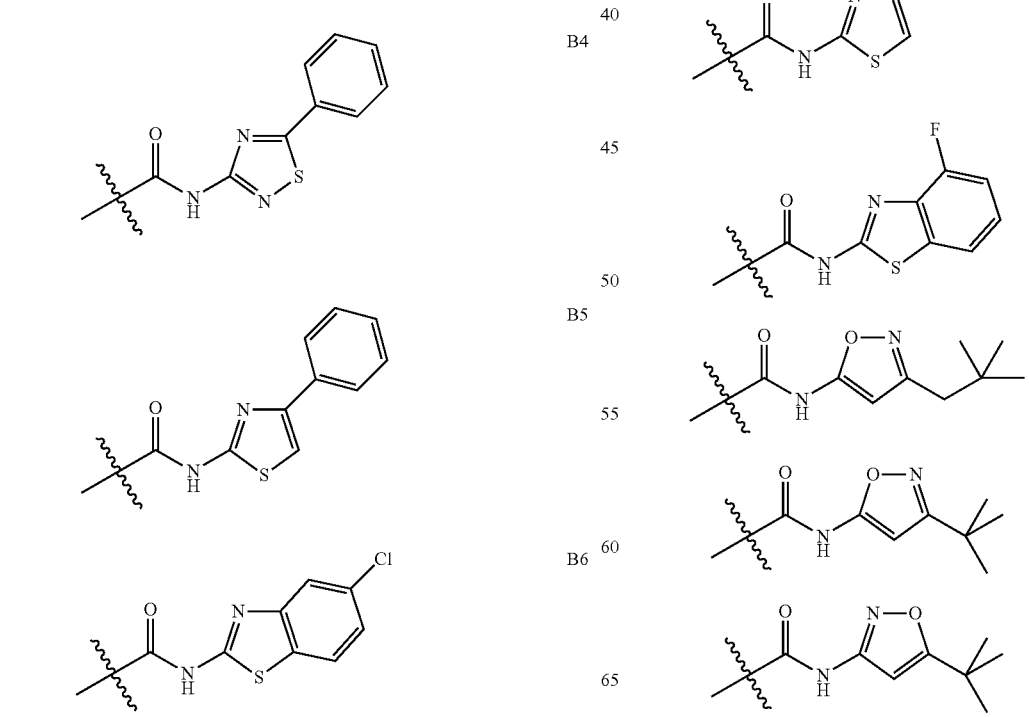

TABLE I-continued

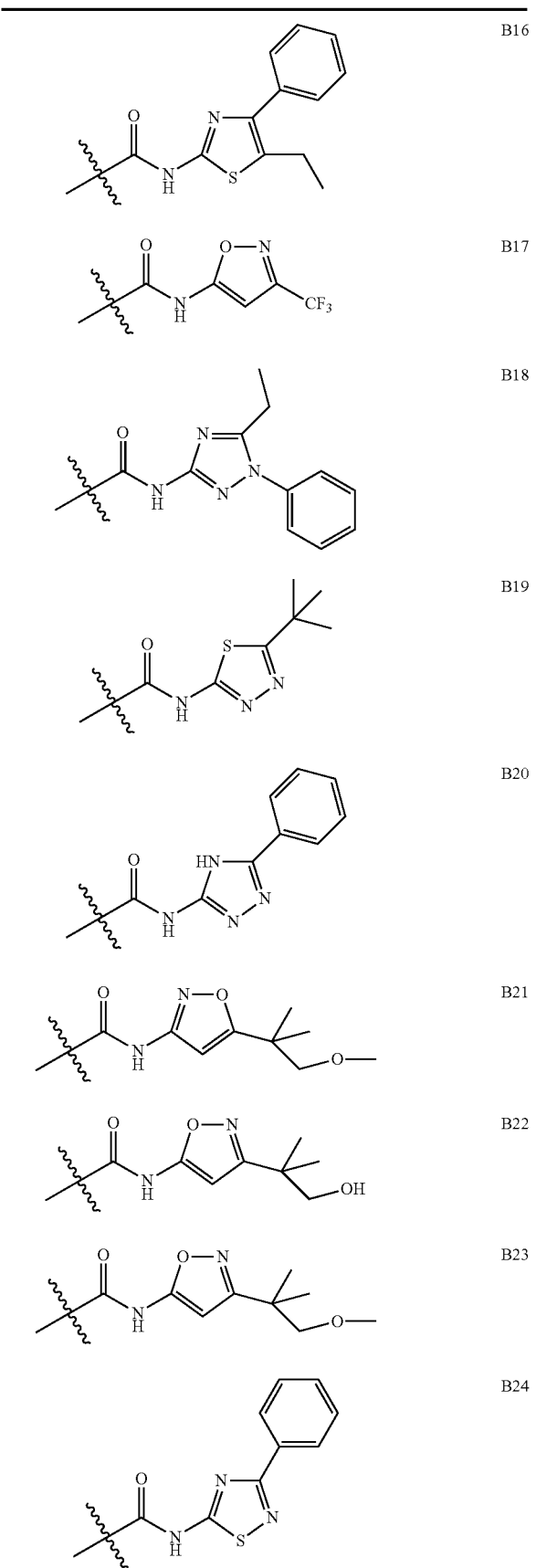

TABLE I-continued

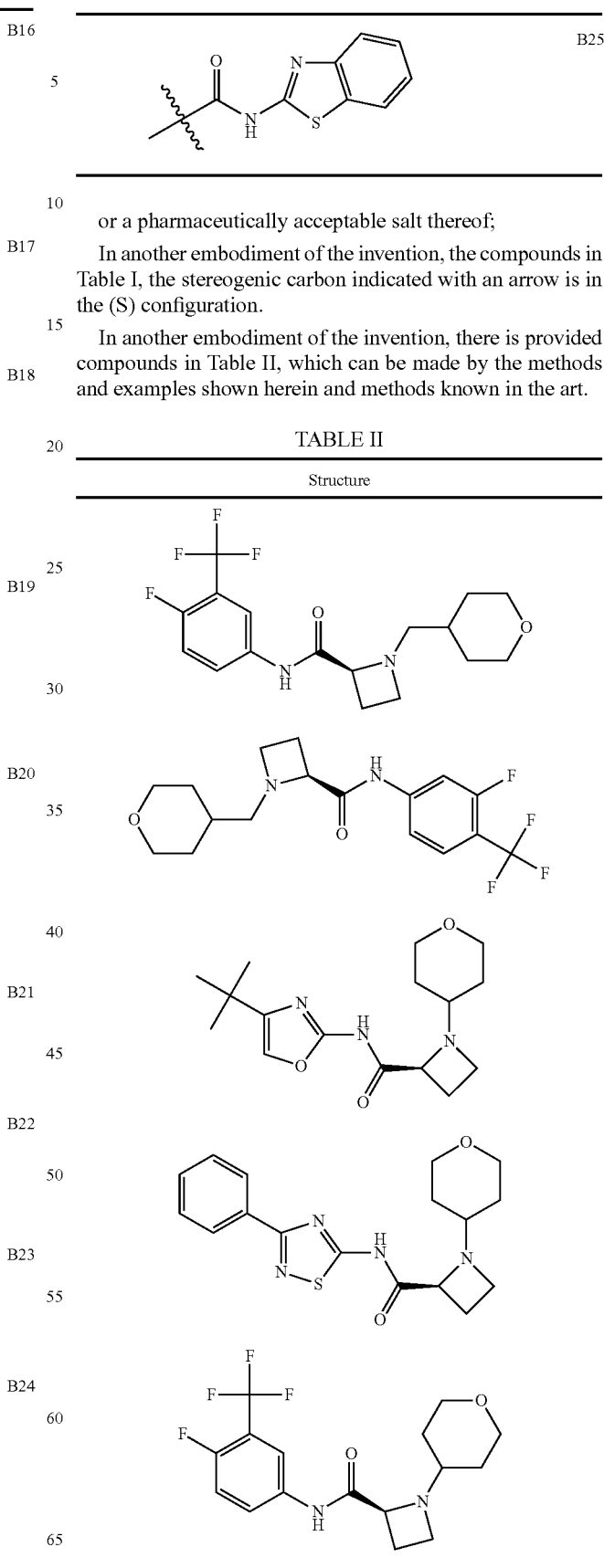

or a pharmaceutically acceptable salt thereof;

In another embodiment of the invention, the compounds in Table I, the stereogenic carbon indicated with an arrow is in the (S) configuration.

In another embodiment of the invention, there is provided compounds in Table II, which can be made by the methods and examples shown herein and methods known in the art.

TABLE II

Structure

TABLE II-continued
Structure
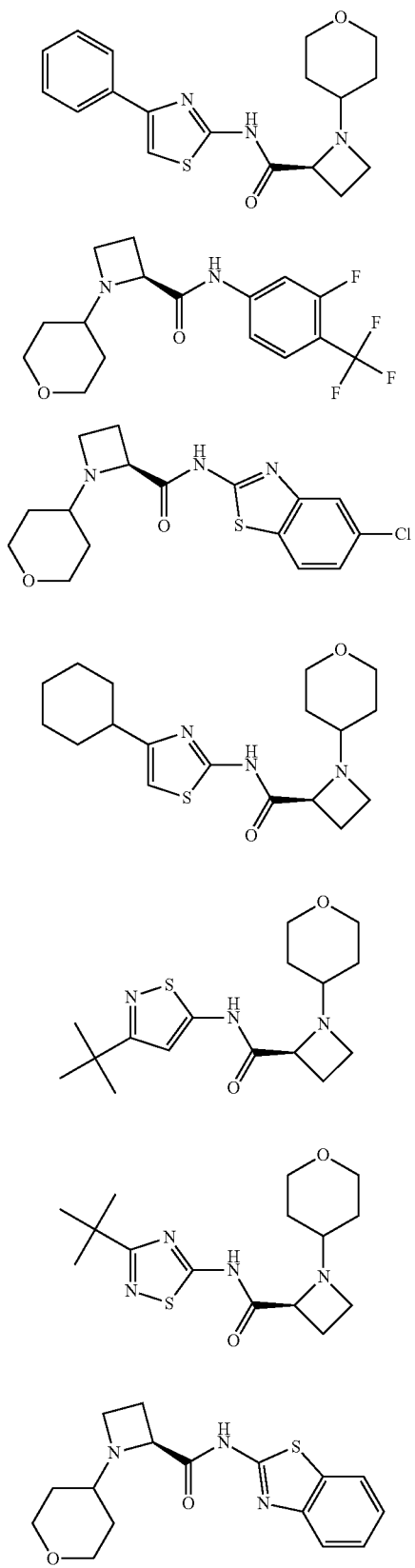
TABLE II-continued
Structure
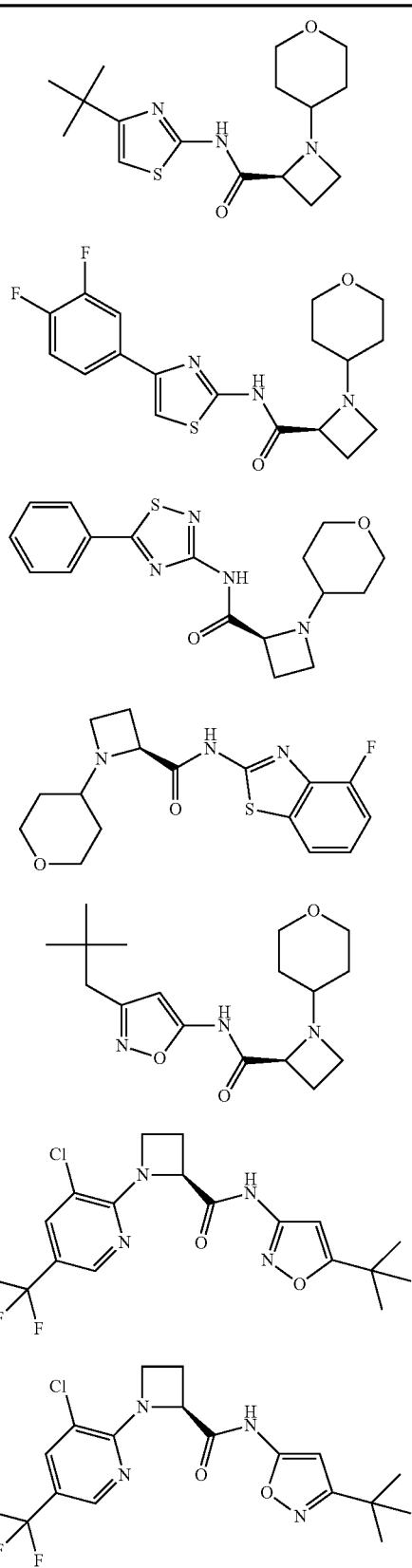

TABLE II-continued
Structure
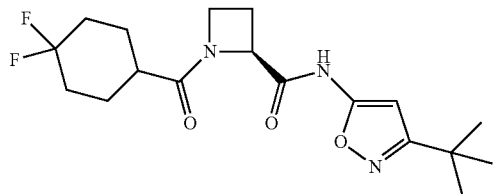 [SMILES: CC(C)(C)c1cc(NC(=O)[C@@H]2CCN2C(=O)C2CCC(F)(F)CC2)on1]
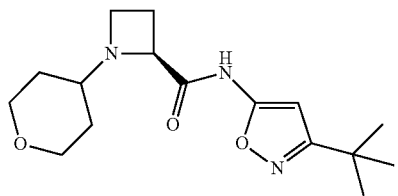
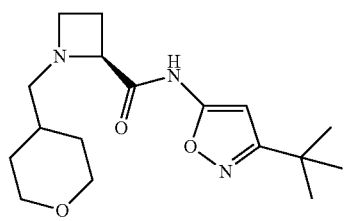
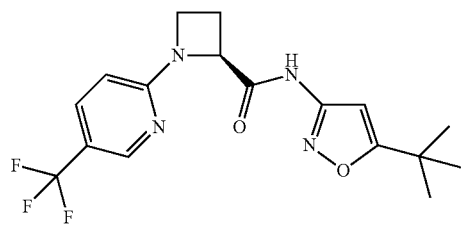 [SMILES: CC(C)(C)c1cc(NC(=O)[C@@H]2CCN2c2ccc(C(F)(F)F)cn2)no1]
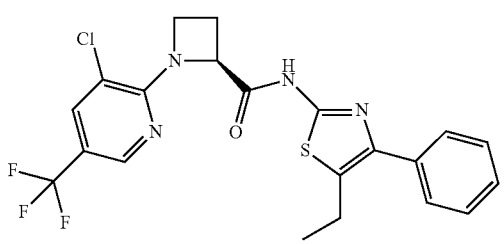 [SMILES: CCc1sc(NC(=O)[C@@H]2CCN2c2ncc(C(F)(F)F)cc2Cl)nc1-c1ccccc1]
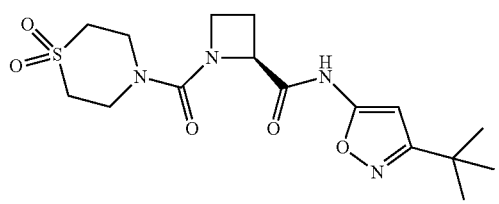 [SMILES: CC(C)(C)c1cc(NC(=O)[C@@H]2CCN2C(=O)N2CCS(=O)(=O)CC2)on1]
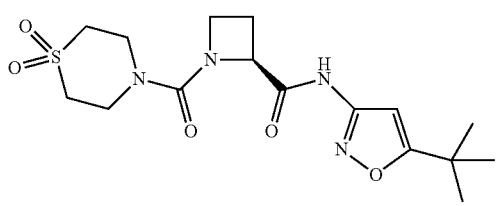 [SMILES: CC(C)(C)c1cc(NC(=O)[C@@H]2CCN2C(=O)N2CCS(=O)(=O)CC2)no1]
TABLE II-continued
Structure
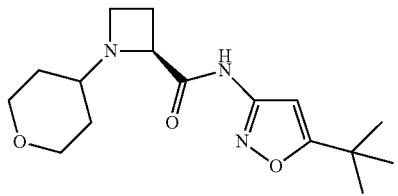 [SMILES: CC(C)(C)c1cc(NC(=O)[C@@H]2CCN2C2CCOCC2)no1]
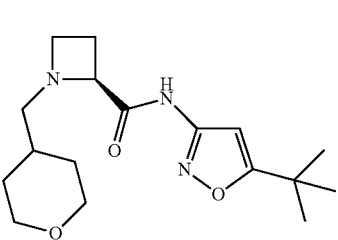 [SMILES: CC(C)(C)c1cc(NC(=O)[C@@H]2CCN2CC2CCOCC2)no1]
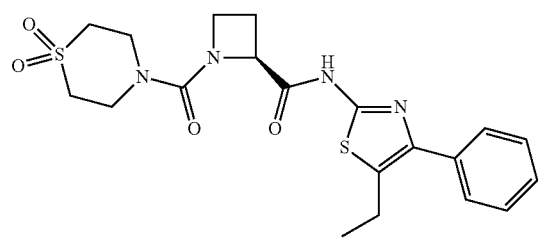 [SMILES: CCc1sc(NC(=O)[C@@H]2CCN2C(=O)N2CCS(=O)(=O)CC2)nc1-c1ccccc1]
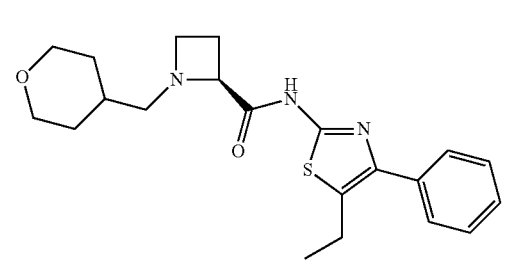 [SMILES: CCc1sc(NC(=O)[C@@H]2CCN2CC2CCOCC2)nc1-c1ccccc1]
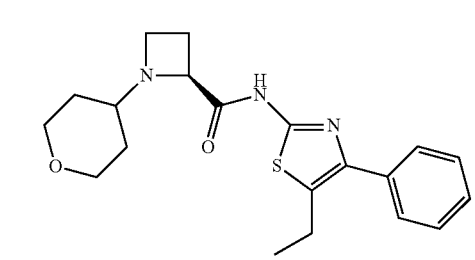 [SMILES: CCc1sc(NC(=O)[C@@H]2CCN2C2CCOCC2)nc1-c1ccccc1]
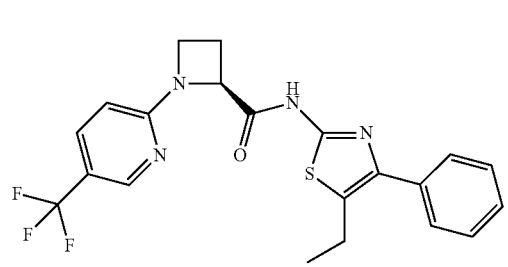 [SMILES: CCc1sc(NC(=O)[C@@H]2CCN2c2ccc(C(F)(F)F)cn2)nc1-c1ccccc1]

TABLE II-continued

Structure (structures only)

TABLE II-continued
Structure
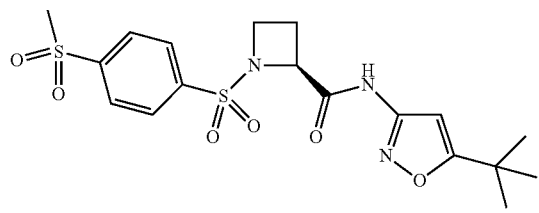 [SMILES: CC(C)(C)c1cc(NC(=O)[C@@H]2CCN2S(=O)(=O)c2ccc(S(C)(=O)=O)cc2)no1]
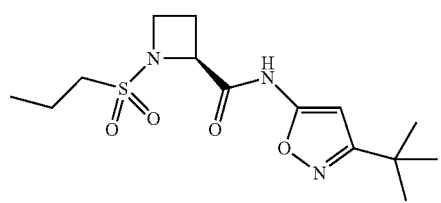
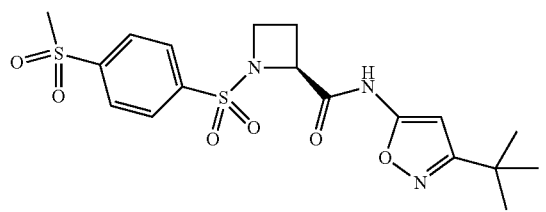 [SMILES: CC(C)(C)c1cc(NC(=O)[C@@H]2CCN2S(=O)(=O)c2ccc(S(C)(=O)=O)cc2)on1]
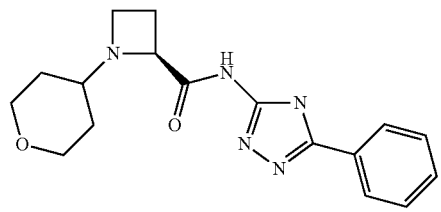 [SMILES: O=C(Nc1nnc(-c2ccccc2)[nH]1)[C@@H]1CCN1C1CCOCC1]
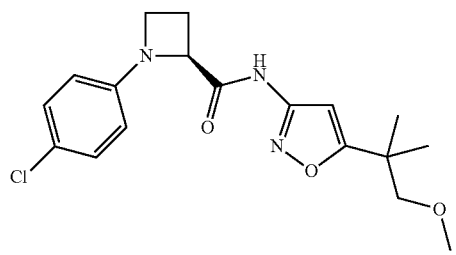 [SMILES: COCC(C)(C)c1cc(NC(=O)[C@@H]2CCN2c2ccc(Cl)cc2)no1]
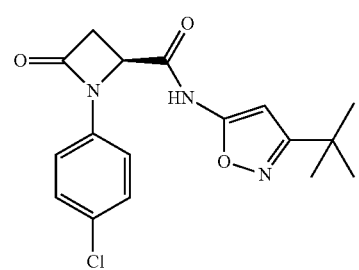 [SMILES: CC(C)(C)c1cc(NC(=O)[C@@H]2CC(=O)N2c2ccc(Cl)cc2)on1]
TABLE II-continued
Structure
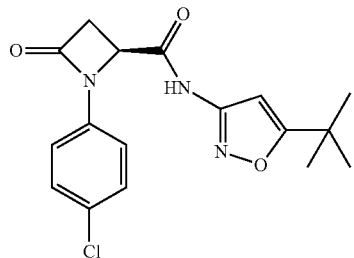 [SMILES: CC(C)(C)c1cc(NC(=O)[C@@H]2CC(=O)N2c2ccc(Cl)cc2)no1]
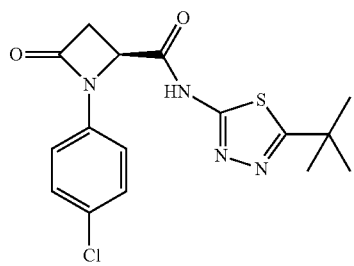 [SMILES: CC(C)(C)c1nnc(NC(=O)[C@@H]2CC(=O)N2c2ccc(Cl)cc2)s1]
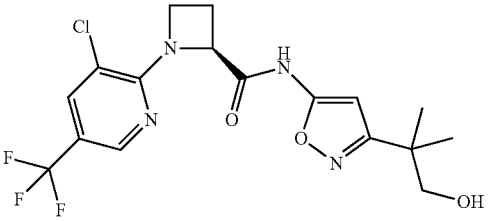 [SMILES: CC(C)(CO)c1cc(NC(=O)[C@@H]2CCN2c2ncc(C(F)(F)F)cc2Cl)on1]
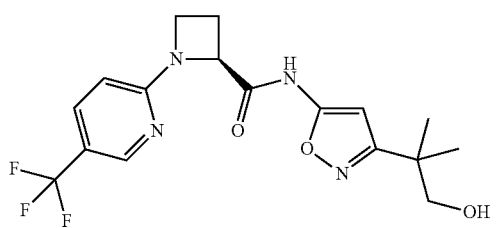 [SMILES: CC(C)(CO)c1cc(NC(=O)[C@@H]2CCN2c2ccc(C(F)(F)F)cn2)on1]
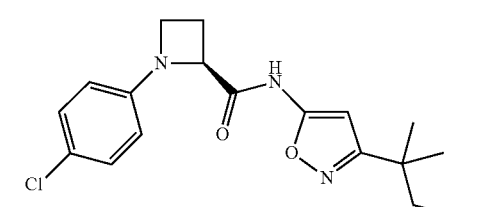
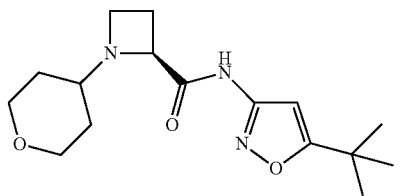 [SMILES: CC(C)(C)c1cc(NC(=O)[C@@H]2CCN2C2CCOCC2)no1]

TABLE II-continued

Structure

[Chemical structures omitted]

or a pharmaceutically acceptable salt thereof.

Of the above compounds, the following are preferred CB2 agonists:

TABLE III

| Compound | CB2 EC$_{50}$ (nM) |
|---|---|
| [structure] | 206 |
| [structure] | 465 |
| [structure] | 371 |
| [structure] | 86 |
| [structure] | 56 |
| [structure] | 313 |

TABLE III-continued

| Compound | CB2 EC50 (nM) |
|---|---|
| (3-tert-butyl-1,2,4-thiadiazol-5-yl / tetrahydropyran-azetidine amide) | 471 |
| (3,4-difluorophenyl thiazole / tetrahydropyran-azetidine amide) | 203 |
| (tetrahydropyran-azetidine / 4-fluorobenzothiazole amide) | 153 |
| (neopentyl-isoxazole / tetrahydropyran-azetidine amide) | 243 |
| (3-chloro-5-trifluoromethylpyridine-azetidine / 5-tert-butylisoxazole amide) | 0.02 |
| (3-chloro-5-trifluoromethylpyridine-azetidine / 5-tert-butylisoxazole amide, isomer) | 0.05 |
| (4,4-difluorocyclohexanoyl-azetidine / 5-tert-butylisoxazole amide) | 127 |

| Compound | CB2 EC50 (nM) |
|---|---|
| (tetrahydropyran-azetidine / 5-tert-butylisoxazole amide) | 8.8 |
| (tetrahydropyranylmethyl-azetidine / 5-tert-butylisoxazole amide) | 35 |
| (5-trifluoromethylpyridine-azetidine / 5-tert-butylisoxazole amide) | 1.1 |
| (3-chloro-5-trifluoromethylpyridine-azetidine / 5-ethyl-4-phenylthiazole amide) | 2.7 |
| (tetrahydropyran-azetidine / 5-tert-butylisoxazole amide) | 18 |
| (tetrahydropyranylmethyl-azetidine / 5-tert-butylisoxazole amide) | 4.3 |
| (tetrahydropyranylmethyl-azetidine / 5-ethyl-4-phenylthiazole amide) | 4.1 |

TABLE III-continued

| Compound | CB2 EC$_{50}$ (nM) |
|---|---|
| [tetrahydropyran-azetidine-C(O)NH-thiazole(Ph)(Et)] | 116 |
| [5-CF$_3$-pyridin-2-yl-azetidine-C(O)NH-thiazole(Ph)(Et)] | 128 |
| [5-CF$_3$-pyridin-2-yl-azetidine-C(O)NH-isoxazole(tBu)] | 0.67 |
| [4-Cl-phenyl-azetidine-C(O)NH-isoxazole(tBu)] (3-position) | 1.7 |
| [4-Cl-phenyl-azetidine-C(O)NH-isoxazole(tBu)] (5-position) | 0.75 |
| [4-Cl-phenyl-azetidine-C(O)NH-isoxazole(CF$_3$)] | 43 |
| [isopropyl-azetidine-C(O)NH-isoxazole(tBu)] | 26 |
| [cyclopentyl-azetidine-C(O)NH-isoxazole(tBu)] | 6.6 |
| [cyclohexyl-azetidine-C(O)NH-isoxazole(tBu)] | 0.08 |
| [3,4-difluorobenzyl-azetidine-C(O)NH-isoxazole(tBu)] | 14 |
| [4-(methylsulfonyl)phenylsulfonyl-azetidine-C(O)NH-isoxazole(tBu)] (3-position) | 197 |
| [propylsulfonyl-azetidine-C(O)NH-isoxazole(tBu)] | 157 |
| [4-(methylsulfonyl)phenylsulfonyl-azetidine-C(O)NH-isoxazole(tBu)] (5-position) | 357 |
| [4-Cl-phenyl-azetidine-C(O)NH-isoxazole(CMe$_2$CH$_2$OMe)] | 12 |

TABLE III-continued

| Compound | CB2 EC$_{50}$ (nM) |
|---|---|
| 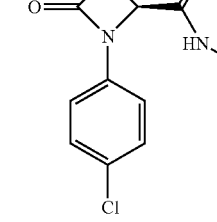 | 17 |
| 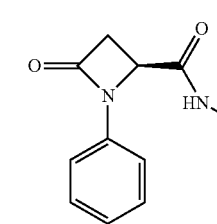 | 50 |
| 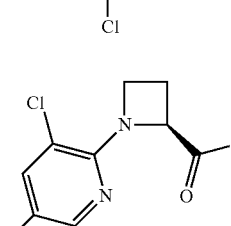 | 0.12 |
| 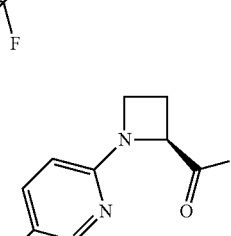 | 18 |
| 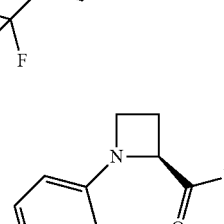 | 18 |
| 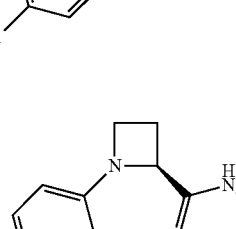 | 22 |
| (structure) | 7.7 |
| (structure) | 5.6 |
| (structure) | 75 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$ alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocyclic or cycloalkyl groups include hydrocarbon rings containing from three to twelve carbon atoms. These carbocyclic or cycloalkyl groups may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N,O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, tetrahydrothiopyranyl, tetrahydrothienyl, tetrahydrothiopyranyl 1,1-dioxide, tetrahydrothienyl 1,1-dioxide, oxazolyl, isoxazolyl, oxadiazolyl, triazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, quinolinyl, Dihydro-2H-quinolinyl, isoquinolinyl, quinazolinyl, indazolyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle as defined herein. Each aryl unless otherwise specified includes it's partially or fully hydrogenated derivative. For example, naphthyl may include its hydrogenated derivatives such as tetrahydranaphthyl. Other partially or fully hydrogenated derivatives of the aryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention may be made using the general synthetic methods described below, which also constitute part of the invention.

General Synthetic Methods

The invention also provides processes for making compounds of Formula (I), (II) and (III). In all Schemes, unless specified otherwise, $R_1$, $L_1$, $L_2$, $Ar_1$ and $Ar_2$ in the Formulas below shall have the meaning of $R_1$, $L_1$, $L_2$, $Ar_1$ and $Ar_2$ in Formula (I), (II) and (III) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

Compounds of Formula (I) and (III) may be synthesized by the method outlined in scheme 1.

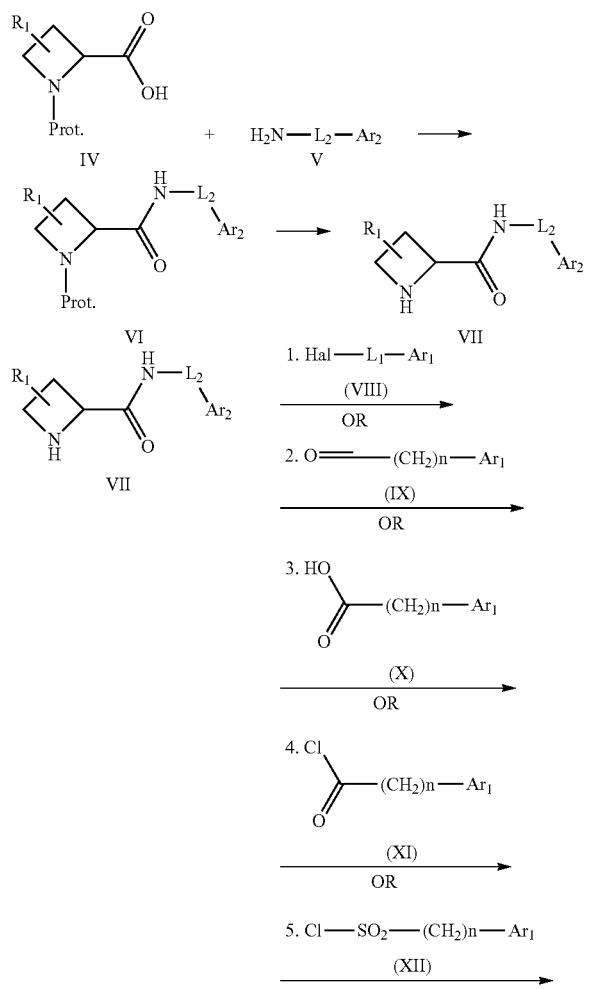

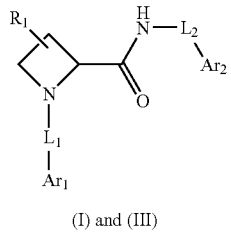

$L_1$ = a bond, —$CH_2(CH_2)n$—,

—$C(O)$—$(CH_2)n$—, —$SO_2$—$(CH_2)n$— n = 0, 1, 2 or 3

As illustrated in scheme 1, reaction of an appropriately substituted azetidine carboxylic acid (IV) with an amine of formula (V), under standard coupling conditions and as described in the examples, provides an amide of formula (VI). Prot.=amine protecting group, such as BOC. Reaction of the intermediate (VI) with an acid such as hydrochloric acid, in a suitable solvent, provides the deprotected amine intermediate (VII). Reaction of the intermediate (VII) with a suitable halide Hal-$L_1$-$Ar_1$ (VIII), wherein Hal=F, Cl, Br or I, in a suitable solvent, in the presence of a suitable base, provides a compound of Formula (I). Intermediate (VII) may also be reacted with a carbonyl compound of formula (IX) under reductive amination conditions, to provide a compound of Formula (I).

Alternatively, reaction of the intermediate (VII) with an acid of formula (X) under standard coupling conditions, provides a compound of Formula (I). Reaction of intermediate (VII) with an acid chloride of formula (XI) or a sulfonyl chloride of formula (XII), under standard reaction conditions, provides the corresponding compound of Formula (I). Compounds of Formula (III) may be synthesized using the procedure outlined in scheme 1, and as described in the examples.

Compounds of Formula (I) and (III) may also be prepared according to scheme 2.

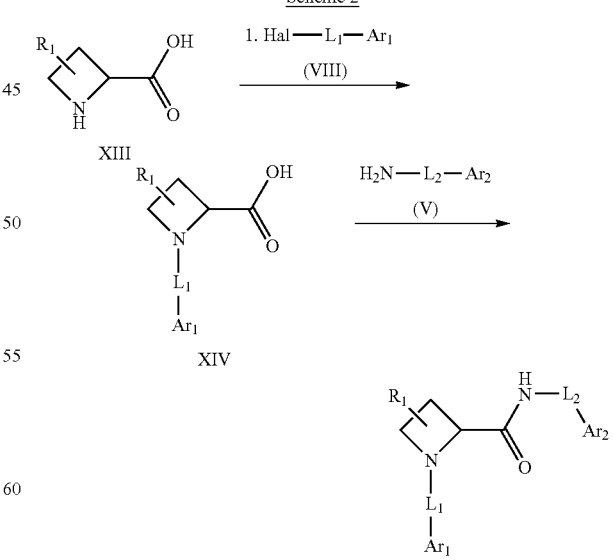

As outlined in scheme 2, reaction of the azetidine carboxylic acid starting material of formula (XIII) with a suitable halide Hal-L$_1$-Ar$_1$ (VIII), wherein Hal=F, Cl, Br or I, in a suitable solvent, in the presence of a suitable base, provides a compound of formula (XIV). Reaction of intermediate (XIV) with an amine of formula (V), under standard coupling conditions and as described in coupling methods in examples, provides a compound of Formula (I).

Compounds of Formula (II) may be made according to scheme 3.

Scheme 3

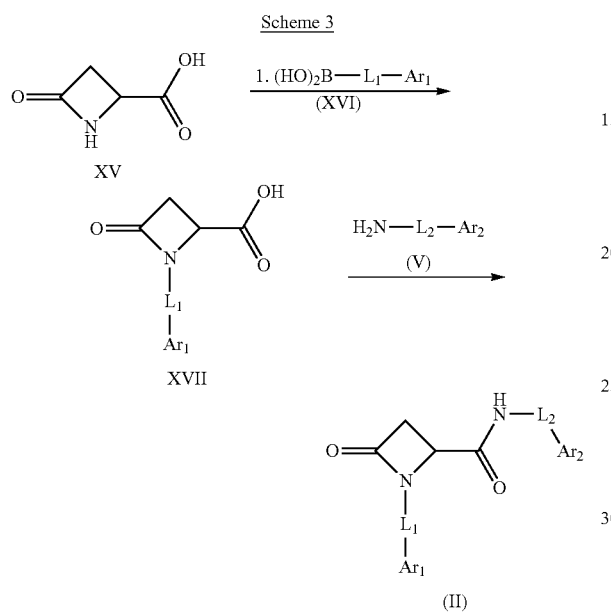

As illustrated in scheme 3, reaction of an appropriately substituted azetidinone carboxylic acid (XV) with a boronic acid or ester of formula (XVI), under standard arylation conditions, provides an acid of formula (XVII). Reaction of acid (XVII) with an amine of formula (V), under standard coupling conditions or via an acid chloride, provides a compound of Formula (II).

Further modification of the initial product of Formula (I), (II) and (III) by methods known to one skilled in the art and illustrated in the examples below, provides additional compounds of this invention.

EXAMPLES

Compounds of Formula (I) and (III)
Method A

Synthesis of (S)-1-(3-Chloro-5-trifluoromethyl-pyridin-2-yl)-azetidine-2-carboxylic acid (5-tert-butyl-isoxazol-3-yl)-amide (Example 18)

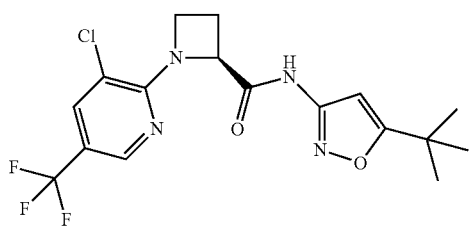

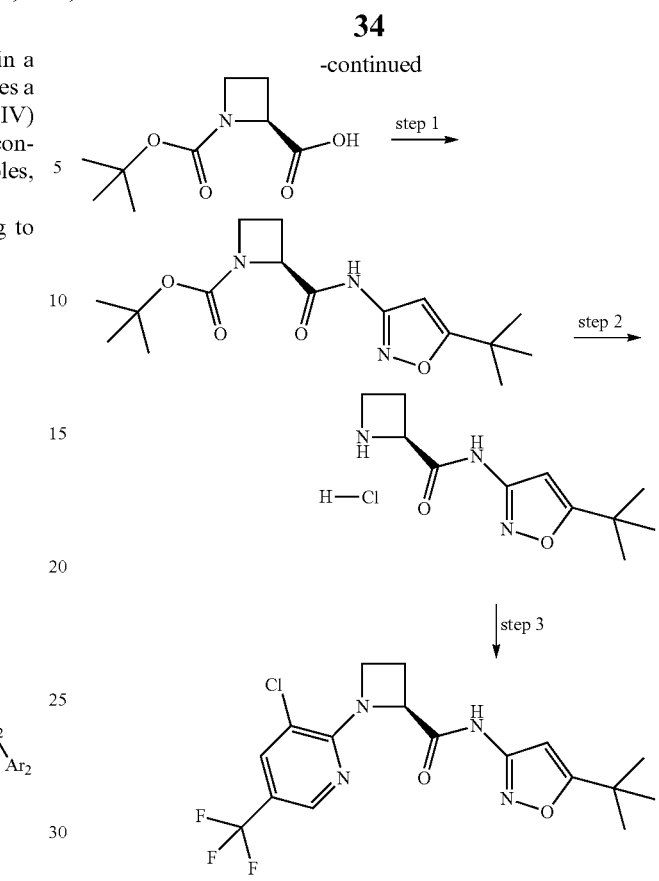

Step 1: Synthesis of (S)-2-(5-tert-Butyl-isoxazol-3-ylcarbamoyl)-azetidine-1-carboxylic acid tert-butyl ester

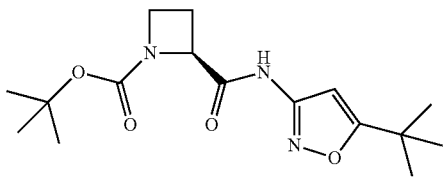 [SMILES: CC(C)(C)OC(=O)N1CC[C@H]1C(=O)Nc1cc(C(C)(C)C)on1]

Two different amide coupling procedures can be used for step 1. Amide intermediates and the coupling procedures 1-2 to synthesize them are listed in Table 1.

Amide Coupling Procedure 1: Synthesis of (S)-2-(5-tert-Butyl-isoxazol-3-ylcarbamoyl)-azetidine-1-carboxylic acid tert-butyl ester

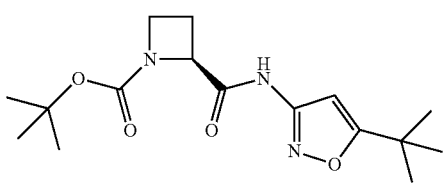 [SMILES: CC(C)(C)OC(=O)N1CC[C@H]1C(=O)Nc1cc(C(C)(C)C)on1]

2-Ethoxy-1-ethoxycarbonyl-1,2-dihydroquinoline (368.5 mg; 1.49 mmol) is added to a mixture of boc-L-azetidine-2- carboxylic acid (200 mg; 0.994 mmol) and 3-amino-5-t-butylisoxazole (139 mg; 0.994 mmol) in toluene (5 mL) at room temperature and the mixture is stirred for 18 hours. After this time, the reaction mixture is quenched with water and extracted with ethyl acetate twice. The organics are combined and washed with brine, dried over Na2SO4, filtered and concentrated in vacuo. Purification by flash chromatography on silica gel using methanol/methylene chloride provides the title compound, m/z 324 [M+H⁺].

Amide Coupling Procedure 2: Synthesis of (S)-2-(5-tert-Butyl-isoxazol-3-ylcarbamoyl)-azetidine-1-carboxylic acid tent-butyl ester

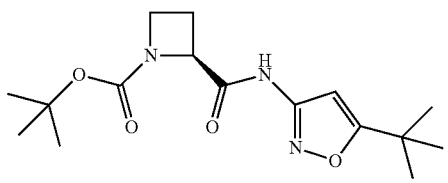 [SMILES: CC(C)(C)OC(=O)N1CC[C@H]1C(=O)Nc1cc(C(C)(C)C)on1]

To a cold (5° C.) solution of boc-L-azetidine-2-carboxylic acid (500 mg; 2.485 mmol) and 3-amino-5-t-butylisoxazole (348 mg; 2.485 mmol) in anhydrous pyridine (5 mL) is added phosphorus oxychloride (0.246 mL; 2.73 mmol). The reaction mixture is left stifling and allowed to warm to room temperature for 18 hours. After this time, the reaction mixture is quenched with saturated ammonium chloride aqueous solution and extracted with ethyl acetate twice. The organics are combined and washed with brine, dried over Na2SO4, filtered and concentrated in vacuo. Purification by flash chromatography on silica gel using ethyl acetate/hexanes provides the title compound, m/z 324 [M+H⁺].

TABLE 1

Amide Intermediates

| Structure | m/z [M + H⁺] | Coupling Procedure |
|---|---|---|
| | 324 | 1, 2 |
| | 324 | 2 |
| 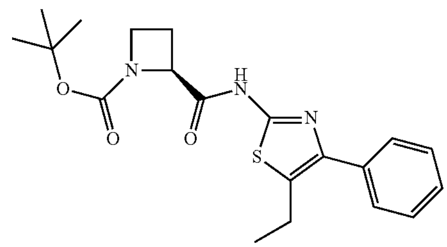 [SMILES: CCc1sc(NC(=O)[C@@H]2CCN2C(=O)OC(C)(C)C)nc1-c1ccccc1] | 388 | 2 |
| 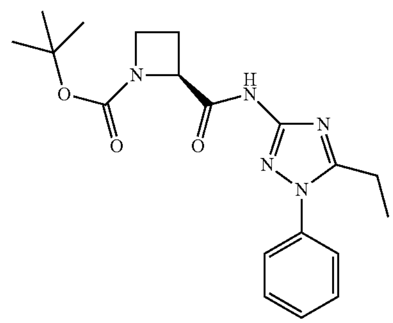 [SMILES: CCc1nc(NC(=O)[C@@H]2CCN2C(=O)OC(C)(C)C)nn1-c1ccccc1] | 372 | 2 |
| 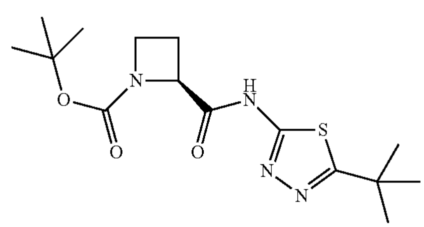 [SMILES: CC(C)(C)OC(=O)N1CC[C@H]1C(=O)Nc1nnc(C(C)(C)C)s1] | 341 | 2 |
| 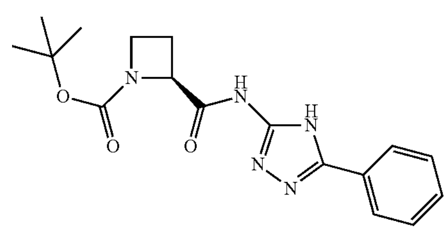 [SMILES: CC(C)(C)OC(=O)N1CC[C@H]1C(=O)Nc1nnc(-c2ccccc2)[nH]1] | 344 | 2 |
| 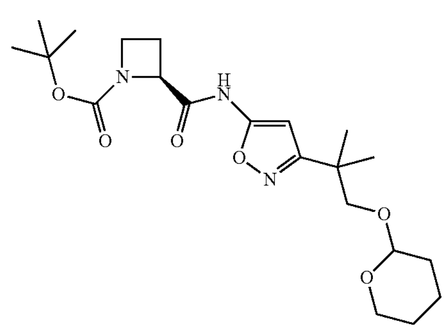 [SMILES: CC(C)(C)OC(=O)N1CC[C@H]1C(=O)Nc1cc(C(C)(C)COC2CCCCO2)no1] | 424 | 2 |

TABLE 1-continued
Amide Intermediates
| Structure | m/z [M + H+] | Coupling Procedure |
|---|---|---|
| 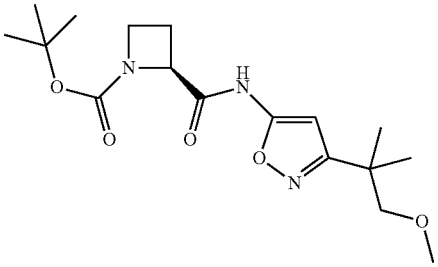 [SMILES: COCC(C)(C)c1cc(NC(=O)[C@@H]2CCN2C(=O)OC(C)(C)C)on1] | 354 | 2 |
| 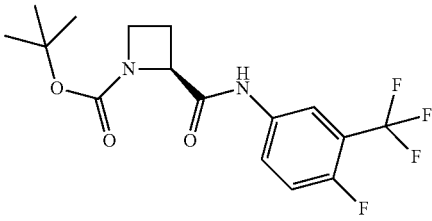 [SMILES: CC(C)(C)OC(=O)N1CC[C@H]1C(=O)Nc1ccc(F)c(C(F)(F)F)c1] | 363 | 1 |
| 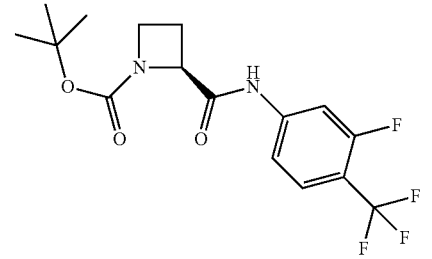 [SMILES: CC(C)(C)OC(=O)N1CC[C@H]1C(=O)Nc1ccc(C(F)(F)F)c(F)c1] | 363 | 1 |
| 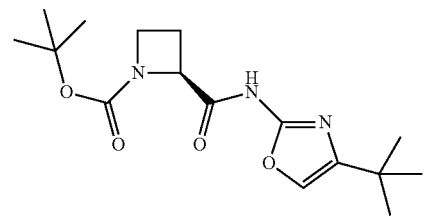 [SMILES: CC(C)(C)OC(=O)N1CC[C@H]1C(=O)Nc1nc(C(C)(C)C)co1] | 324 | 1 |
| 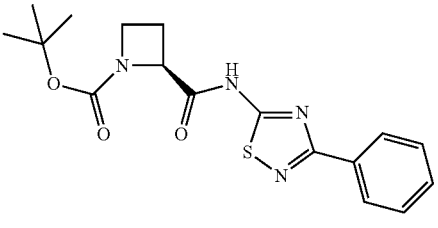 [SMILES: CC(C)(C)OC(=O)N1CC[C@H]1C(=O)Nc1nc(-c2ccccc2)ns1] | 361 | 1 |
| 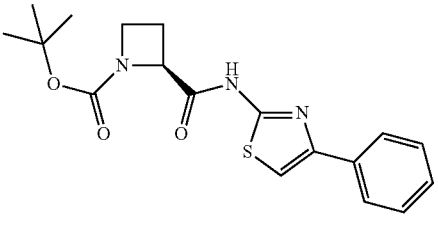 [SMILES: CC(C)(C)OC(=O)N1CC[C@H]1C(=O)Nc1nc(-c2ccccc2)cs1] | 360 | 1 |
TABLE 1-continued
Amide Intermediates
| Structure | m/z [M + H+] | Coupling Procedure |
|---|---|---|
| 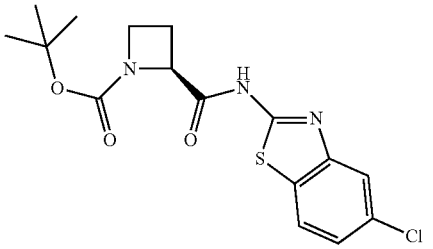 [SMILES: CC(C)(C)OC(=O)N1CC[C@H]1C(=O)Nc1nc2cc(Cl)ccc2s1] | 368 | 1 |
| 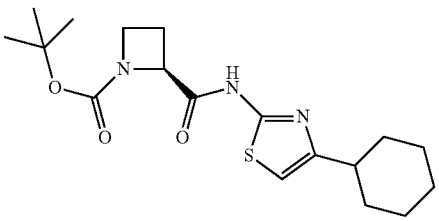 [SMILES: CC(C)(C)OC(=O)N1CC[C@H]1C(=O)Nc1nc(C2CCCCC2)cs1] | 366 | 1 |
| 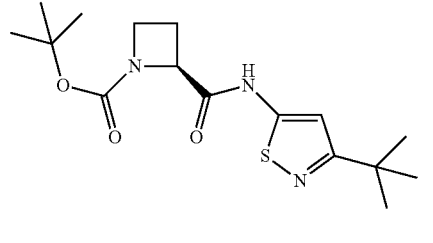 [SMILES: CC(C)(C)OC(=O)N1CC[C@H]1C(=O)Nc1cc(C(C)(C)C)ns1] | 340 | 1 |
| 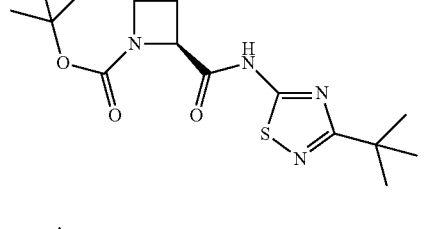 | 341 | 1 |
| 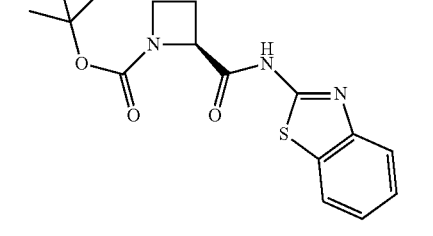 | 334 | 1 |
| 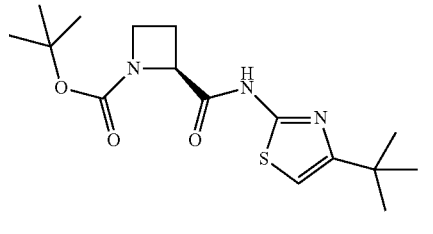 [SMILES: CC(C)(C)OC(=O)N1CC[C@H]1C(=O)Nc1nc(C(C)(C)C)cs1] | 340 | 1 |

TABLE 1-continued

Amide Intermediates

| Structure | m/z [M + H⁺] | Coupling Procedure |
|---|---|---|
| 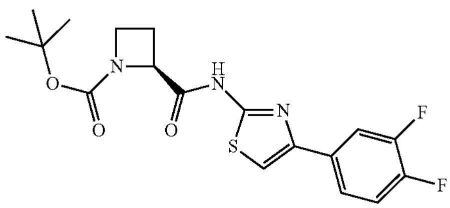 [SMILES: CC(C)(C)OC(=O)N1CC[C@H]1C(=O)Nc1nc(-c2ccc(F)c(F)c2)cs1] | 396 | 1 |
| 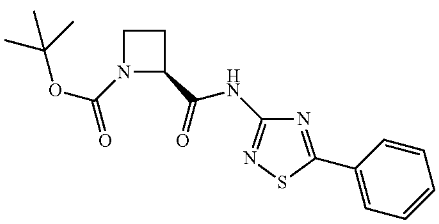 [SMILES: CC(C)(C)OC(=O)N1CC[C@H]1C(=O)Nc1nsc(-c2ccccc2)n1] | 361 | 1 |
| 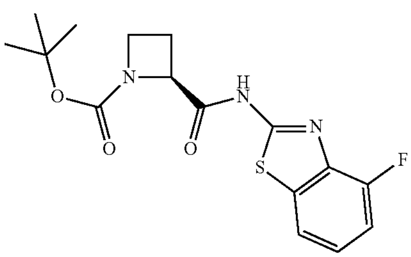 [SMILES: CC(C)(C)OC(=O)N1CC[C@H]1C(=O)Nc1nc2c(F)cccc2s1] | 352 | 1 |
| 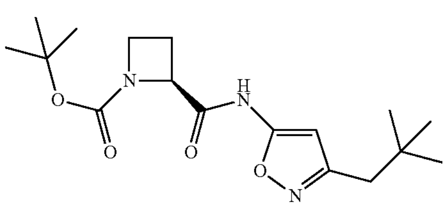 [SMILES: CC(C)(C)Cc1cc(NC(=O)[C@@H]2CCN2C(=O)OC(C)(C)C)on1] | 338 | 1 |
| 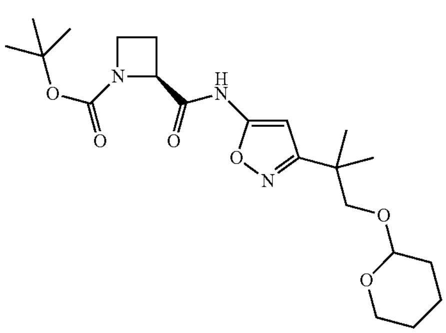 [SMILES: CC(C)(C)OC(=O)N1CC[C@H]1C(=O)Nc1cc(C(C)(C)COC2CCCCO2)no1] | 424 | 2 |

Step 2: Synthesis of (S)-Azetidine-2-carboxylic acid (5-tert-butyl-isoxazol-3-yl)-amide; hydrochloride

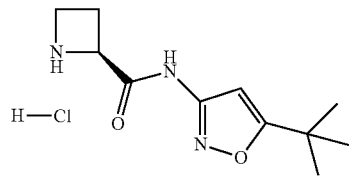

4N HCl in 1,4-dioxane (2.5 mL; 10 mmol) is added to a solution of (S)-2-(5-tert-Butyl-isoxazol-3-ylcarbamoyl)-azetidine-1-carboxylic acid tert-butyl ester (375 mg; 0.829 mmol) in dichloromethane (5 mL). The reaction mixture is stirred at room temperature for 18 hours. After this time, the reaction mixture is concentrated in vacuo to provide the title compound, m/z 224 [M+H⁺].

Intermediates listed in Table 2 are made in a similar manner.

TABLE 2

Amine Salt Intermediates

| Structure | m/z [M + H⁺] |
|---|---|
| | 224 |
| | 224 |
| 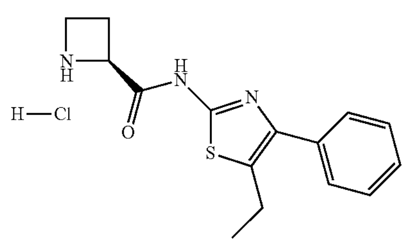 | 288 |
| 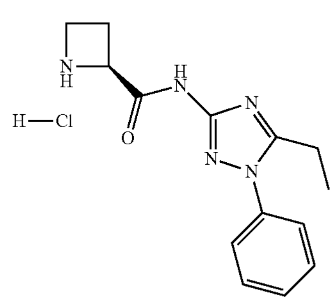 | 272 |

TABLE 2-continued

Amine Salt Intermediates

| Structure | m/z [M + H⁺] |
|---|---|
| (azetidine-2-carboxamide, N-(5-tert-butyl-1,3,4-thiadiazol-2-yl)-, HCl) | 241 |
| (azetidine-2-carboxamide, N-(5-phenyl-4H-1,2,4-triazol-3-yl)-, HCl) | 244 |
| (azetidine-2-carboxamide, N-(3-(2-methyl-1-((tetrahydro-2H-pyran-2-yl)oxy)propan-2-yl)isoxazol-5-yl)-, HCl) | 324 |
| (azetidine-2-carboxamide, N-(3-(1-methoxy-2-methylpropan-2-yl)isoxazol-5-yl)-, HCl) | 254 |
| (azetidine-2-carboxamide, N-(4-fluoro-3-(trifluoromethyl)phenyl)-, HCl) | 263 |
| (azetidine-2-carboxamide, N-(3-fluoro-4-(trifluoromethyl)phenyl)-, HCl) | 263 |

TABLE 2-continued

Amine Salt Intermediates

| Structure | m/z [M + H⁺] |
|---|---|
| (azetidine-2-carboxamide, N-(4-tert-butyloxazol-2-yl)-, HCl) | 224 |
| (azetidine-2-carboxamide, N-(3-phenyl-1,2,4-thiadiazol-5-yl)-, HCl) | 261 |
| (azetidine-2-carboxamide, N-(4-phenylthiazol-2-yl)-, HCl) | 260 |
| (azetidine-2-carboxamide, N-(6-chlorobenzo[d]thiazol-2-yl)-, HCl) | 268 |
| (azetidine-2-carboxamide, N-(4-cyclohexylthiazol-2-yl)-, HCl) | 266 |
| (azetidine-2-carboxamide, N-(3-tert-butylisothiazol-5-yl)-, HCl) | 240 |
| (azetidine-2-carboxamide, N-(3-tert-butyl-1,2,4-thiadiazol-5-yl)-, HCl) | 241 |

TABLE 2-continued

Amine Salt Intermediates

| Structure | m/z [M + H⁺] |
|---|---|
| 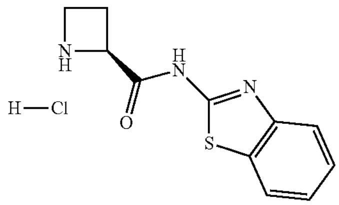 | 234 |
| 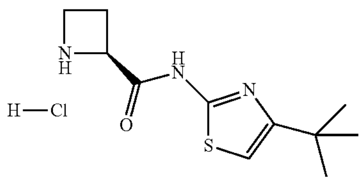 | 240 |
| 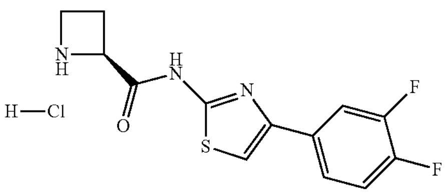 | 296 |
| 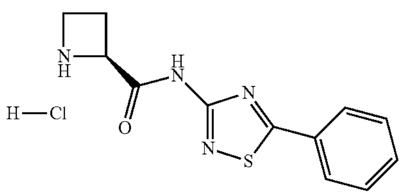 | 261 |
| 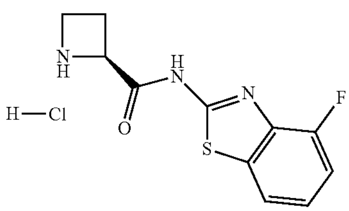 | 252 |
| 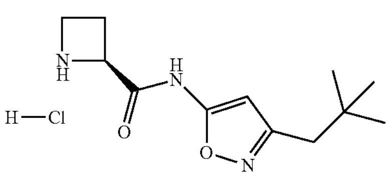 | 238 |
| 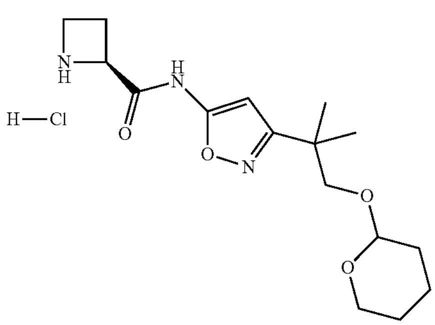 | 324 |

Step 3: Synthesis of (S)-1-(3-Chloro-5-trifluoromethyl-pyridin-2-yl)-azetidine-2-carboxylic acid (5-tent-butyl-isoxazol-3-yl)-amide

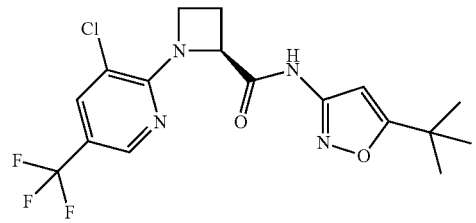

To a stirred solution of (S)-Azetidine-2-carboxylic acid (5-tert-butyl-isoxazol-3-yl)-amide; hydrochloride (61 mg; 0.235 mmol) and N,N-diisopropylethylamine (0.082 mL; 0.47 mmol) in DMSO (1 mL) is added 3-chloro-2-fluoro-5-trifluoromethylpyridine (0.031 mL; 0.235 mmol). The reaction mixture is heated at 100° C. for 1 hour. After this time, the reaction is diluted with ethyl acetate and washed with water twice then brine, dried over Na2SO4, filtered and concentrated in vacuo. Purification by flash chromatography on silica gel using ethyl acetate/hexanes provides the title compound, m/z 403 [M+H⁺].

TABLE 3

Amide Intermediates

| Structure | m/z [M + H⁺] |
|---|---|
| 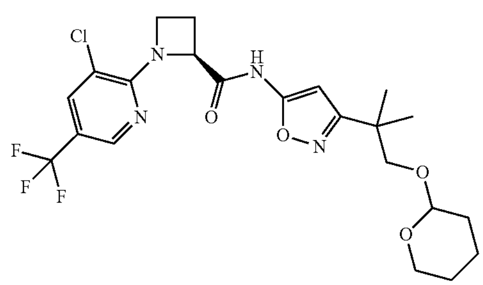 [SMILES: CC(C)(COC1CCCCO1)c1cc(NC(=O)[C@@H]2CCN2c2ncc(C(F)(F)F)cc2Cl)on1] | 503 |
| 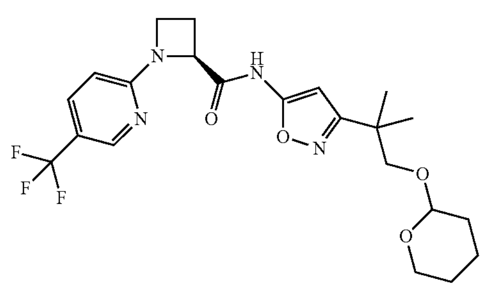 [SMILES: CC(C)(COC1CCCCO1)c1cc(NC(=O)[C@@H]2CCN2c2ccc(C(F)(F)F)cn2)on1] | 469 |

Compounds in Table 6 Method A are prepared in a similar manner.

Method B:

Synthesis of (S)-1-(4,4-Difluoro-cyclohexanecarbonyl)-azetidine-2-carboxylic acid (5-tert-butyl-isoxazol-3-yl)-amide (Example 20)

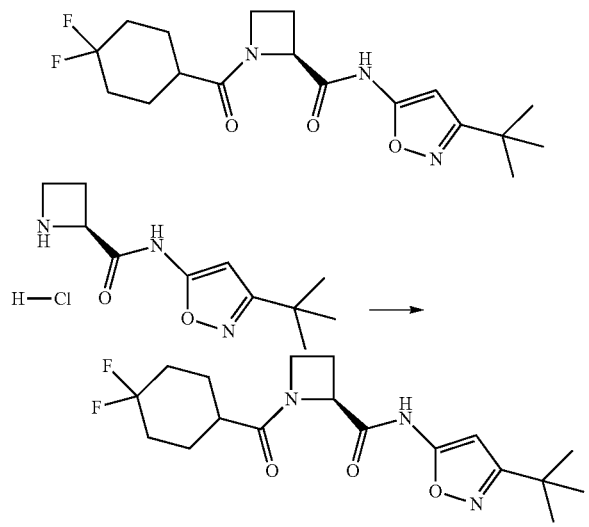

To a solution of 4,4-difluorocyclohexanecarboxylic acid (74.5 mg; 0.454 mmol) and 1-hydroxybenzotriazole hydrate (102 mg; 0.756 mmol) in DMF (1.5 mL) is added 1-(3-dimethylaminopropyl)-3-ethylcarbodiimide hydrochloride (145 mg; 0.756 mmol). After 20 minutes of stirring, (S)-Azetidine-2-carboxylic acid (5-tert-butyl-isoxazol-3-yl)-amide; hydrochloride (150 mg; 0.378 mmol) is added, followed by diisopropylethylamine (0.066 mL; 0.378 mmol) and 4-diemthylaminopyridine (3 mg; 0.025 mmol). The reaction mixture is stirred at room temperature for 1 hour. After this time, the reaction mixture is diluted with ethyl acetate and washed with water, saturated sodium bicarbonate aqueous solution and saturated ammonium chloride aqueous solution then brine, dried over Na2SO4, filtered and concentrated in vacuo. Purification by flash chromatography on silica gel using methanol/methylene chloride provides the title compound, m/z 370 [M+H$^+$].

Compounds in Table 6 Method B are prepared in a similar manner.

Method C:

Three different reductive amination procedures can be used.

Reductive Amination Procedure 1: Synthesis of (S)-1-(Tetrahydro-pyran-4-yl)-azetidine-2-carboxylic acid (3-tert-butyl-isoxazol-5-yl)-amide (Example 21)

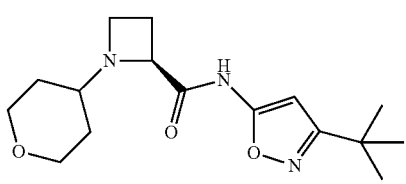

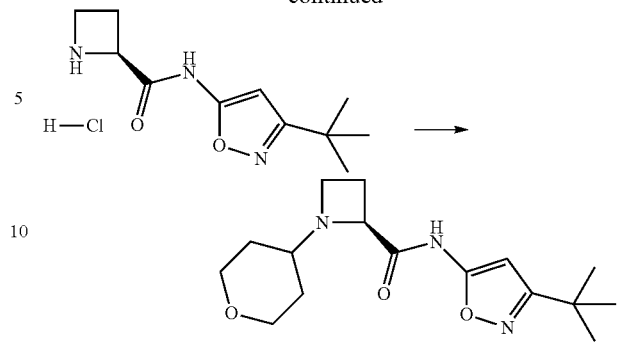

To a solution of (S)-Azetidine-2-carboxylic acid (3-tert-butyl-isoxazol-5-yl)-amide; hydrochloride (78.6 mg; 0.303 mol) in DMF (1 mL) is added tetrahydro-4H-pyran-4-one (0.056 mL; 0.606 mmol) and acetic acid (0.069 mL; 1.212 mmol). The reaction is stirred at room temperature for 50 minutes before adding sodium cyanoborohydride (57 mg; 0.909 mmol). The reaction mixture is left stifling at room temperature for 18 hours. After this time, the reaction mixture is quenched with saturated sodium bicarbonate aqueous solution and extracted with ethyl acetate twice. The organics are combined and washed with brine, dried over Na2SO4, filtered and concentrated in vacuo. Purification by flash chromatography on silica gel using methanol/methylene chloride provides the title compound, m/z 308 [M+H$^+$].

Compounds in Table 6 Method C1 are prepared in a similar manner.

Reductive Amination Procedure 2: Synthesis of (S)-1-(Tetrahydro-pyran-4-ylmethyl)-azetidine-2-carboxylic acid (5-ethyl-4-phenyl-thiazol-2-yl)-amide (Example 30)

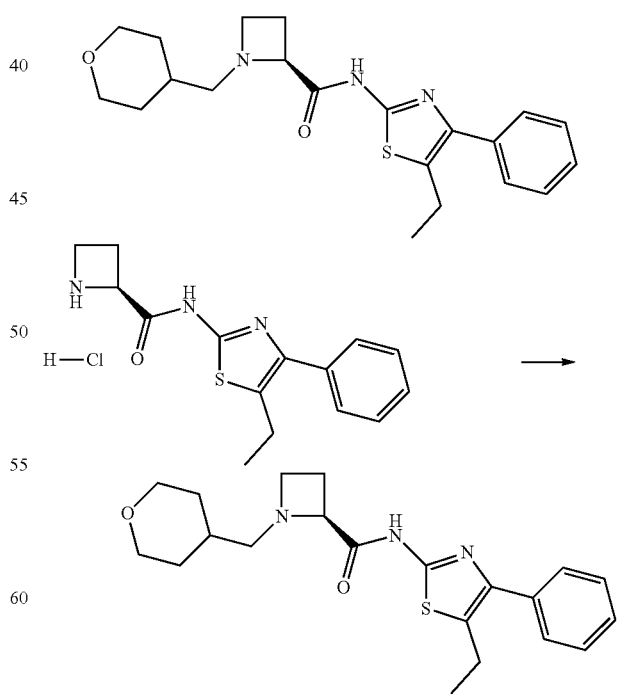

To a suspension of (S)-Azetidine-2-carboxylic acid (5-ethyl-4-phenyl-thiazol-2-yl)-amide; hydrochloride (100 mg; 0.309 mmol) in THF (1.5 mL) id added tetrahydro-pyran- 4-carbaldehyde (70.5 mg; 0.618 mmol), acetic acid (0.071 mL; 1.236 mmol) and MP-cyanoborohydride (327 mg; 2.36 mmol/g). The reaction mixture is agitated at room temperature for 18 hours. After this time, the reaction mixture is filtered and the filtrate is washed with saturated sodium bicarbonate aqueous solution then brine, dried over Na2SO4, filtered and concentrated in vacuo. Purification by flash chromatography on silica gel using methanol/methylene chloride provides the title compound, m/z 386 [M+H$^+$].

Compounds in Table 6 Method C2 are prepared in a similar manner.

Reductive Amination Procedure 3: Synthesis of (S)-1-(Tetrahydro-pyran-4-yl)-azetidine-2-carboxylic acid (3-tert-butyl-isothiazol-5-yl)-amide (Example 10)

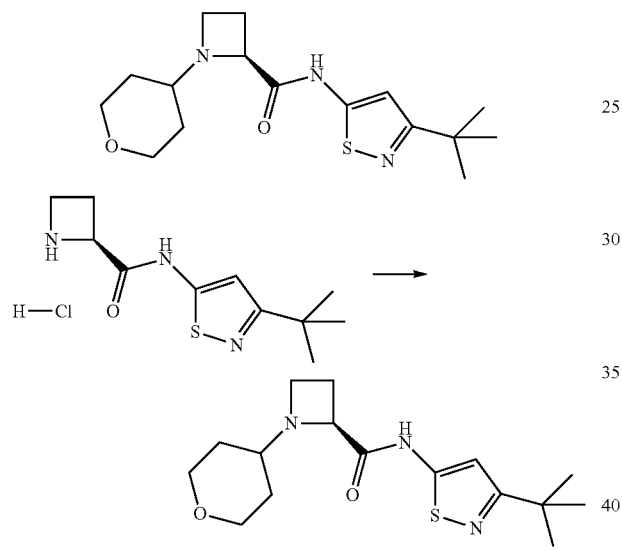

This method is similar to reductive amination procedure 1. The only difference is using sodium triacetoxyborohydride as the reducing reagent instead of sodium cyanoborohyride used in procedure 1.

Compounds in Table 6 Method C3 are prepared in a similar manner.

Method D:

Synthesis of (S)-1-(1,1-Dioxo-1λ$^6$-thiomorpholine-4-carbonyl)-azetidine-2-carboxylic acid (3-tert-butyl-isoxazol-5-yl)-amide (Example 25)

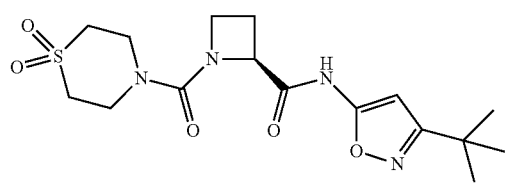

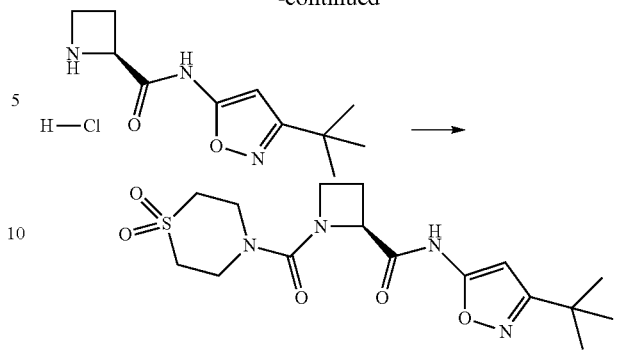

1,1-Dioxo-1λ$^6$-thiomorpholine-4-carbonyl chloride (51.4 mg; 0.26 mmol) is added to a mixture of (S)-Azetidine-2-carboxylic acid (3-tert-butyl-isoxazol-5-yl)-amide; hydrochloride (69 mg; 0.265 mmol) and N,N-diisopropylethylamine (0.141 mL; 0.81 mmol) in THF (2 mL). The reaction mixture is stirred at room temperature for 2 hours. After this time, the reaction mixture is diluted with dichloromethane and washed with water. The layers are separated and the aqueous layer is extracted with dichloromethane once. The organics are combined and washed with brine, dried over Na2SO4, filtered and concentrated in vacuo. Purification by flash chromatography on silica gel using methanol/methylene chloride provides the title compound, m/z 385 [M+H$^+$].

Compounds in Table 6 Method D are prepared in a similar manner.

Method E:

Synthesis of (S)-1-(4-Chloro-phenyl)-azetidine-2-carboxylic acid (5-tert-butyl-isoxazol-3-yl)-amide (Example 35)

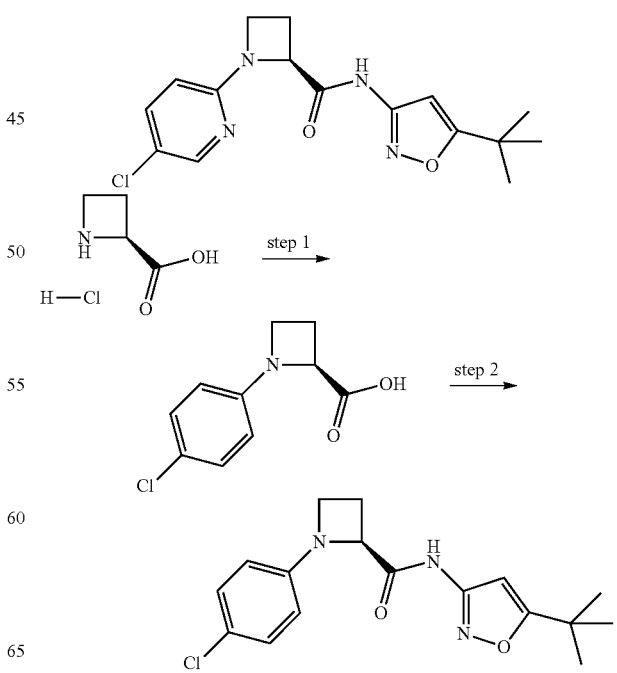

Step 1: Synthesis of (S)-1-(4-Chloro-phenyl)-azetidine-2-carboxylic acid

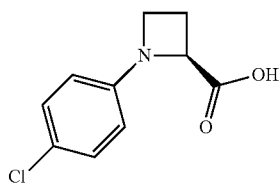 [SMILES: O=C(O)[C@@H]1CCN1c1ccc(Cl)cc1]

A sealed tube is charged with (S)-Azetidine-2-carboxylic acid; hydrochloride (2 g; 19.8 mmol), 4-bromochlorobenzene (3.8 g; 19.8 mmol) and copper iodide (I) (0.38 g; 1.99 mmol) is evacuated and back-filled with Argon 3 times. Dimethylacetamide (40 mL) is added and the tube is sealed and purged with Argon and evacuated 3 times. The sealed tube is heated in 110° C. oil bath for 72 hours. After this time, the reaction mixture is cooled to room temperature and partitioned between ethyl acetate and water. The organic layer is discarded. The aqueous layer is acidified to PH~1 by adding 1N hydrochloric acid and then extracted with ethyl acetate twice. The organics are combined and washed with brine, dried over Na2SO4, filtered and concentrated in vacuo. Purification by flash chromatography on silica gel using methanol/methylene chloride provides the title compound, m/z 212 [M+H$^+$].

TABLE 4

Acid Intermediates

| Structure | m/z [M + H$^+$] |
|---|---|
| 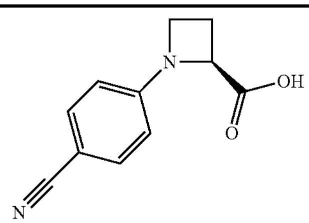 | 203 |
| 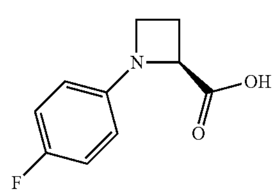 [SMILES: O=C(O)[C@@H]1CCN1c1ccc(F)cc1] | 196 |

Step 2: Synthesis of (S)-1-(4-Chloro-phenyl)-azetidine-2-carboxylic acid (5-tert-butyl-isoxazol-3-yl)-amide

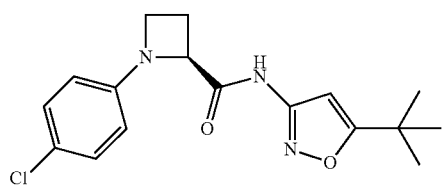 [SMILES: CC(C)(C)c1cc(NC(=O)[C@@H]2CCN2c2ccc(Cl)cc2)no1]

To a cold solution (0° C.) of (S)-1-(4-Chloro-phenyl)-azetidine-2-carboxylic acid (100 mg; 0.472 mmol) and 3-amino-5-t-butylisoxazole (66 mg; 0.472 mmol) in pyridine (1.5 mL) is added phosphorus oxychloride (0.043 m; 0.48 mmol). The reaction mixture is stirred at room temperature for 18 hours. After this time, the reaction mixture is diluted with ethyl acetate and washed with diluted NH4Cl aqueous solution then brine, dried over Na2SO4, filtered and concentrated in vacuo. Purification by flash chromatography on silica gel using ethyl acetate/hexanes provides the title compound, m/z 334 [M+H$^+$].

TABLE 5

Amide Intermediates

| Structure | m/z [M + H$^+$] |
|---|---|
| 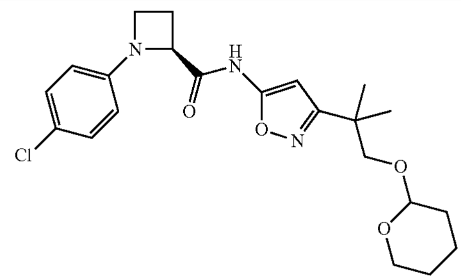 [SMILES: CC(C)(COC1CCCCO1)c1cc(NC(=O)[C@@H]2CCN2c2ccc(Cl)cc2)on1] | 434 |
| 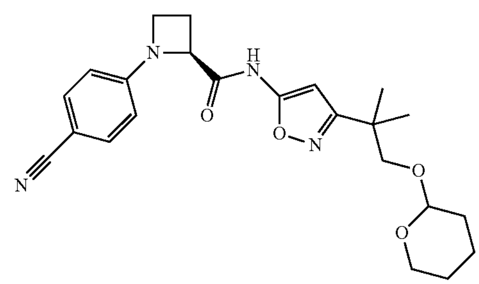 [SMILES: CC(C)(COC1CCCCO1)c1cc(NC(=O)[C@@H]2CCN2c2ccc(C#N)cc2)on1] | 425 |
| 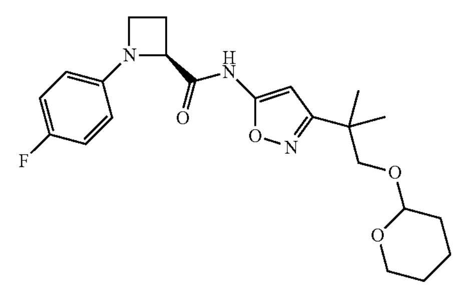 [SMILES: CC(C)(COC1CCCCO1)c1cc(NC(=O)[C@@H]2CCN2c2ccc(F)cc2)on1] | 418 |

Compounds in Table 6 Method E are prepared in a similar manner.

Method F:

Synthesis of (S)-1-(Propane-1-sulfonyl)-azetidine-2-carboxylic acid (5-tert-butyl-isoxazol-3-yl)-amide (Example 45)

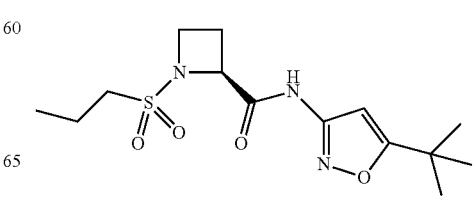

-continued

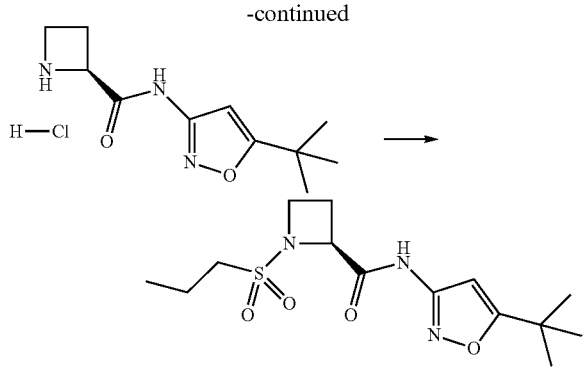

To a solution of (S)-Azetidine-2-carboxylic acid (5-tert-butyl-isoxazol-3-yl)-amide; hydrochloride (100 mg; 0.385 mmol) in DMF (1 mL) is added n-propylsulfonyl chloride (0.043 mL; 0.385 mmol) and N,N-diisopropylethylamine (0.201 mL; 1.155 mmol). The reaction mixture is left stirring at room temperature for 18 hours. After this time, the reaction mixture is diluted with ethyl acetate and washed with water twice then brine, dried over Na2SO4, filtered and concentrated in vacuo. Purification by flash chromatography on silica gel using ethyl acetate/hexanes provides the title compound, m/z 330 [M+H⁺].

Compounds in Table 6 Method F are prepared in a similar manner.

Method G:

Synthesis of (S)-1-(4-Chloro-phenyl)-4-oxo-azetidine-2-carboxylic acid (3-tert-butyl-isoxazol-5-yl)-amide (Example 51)

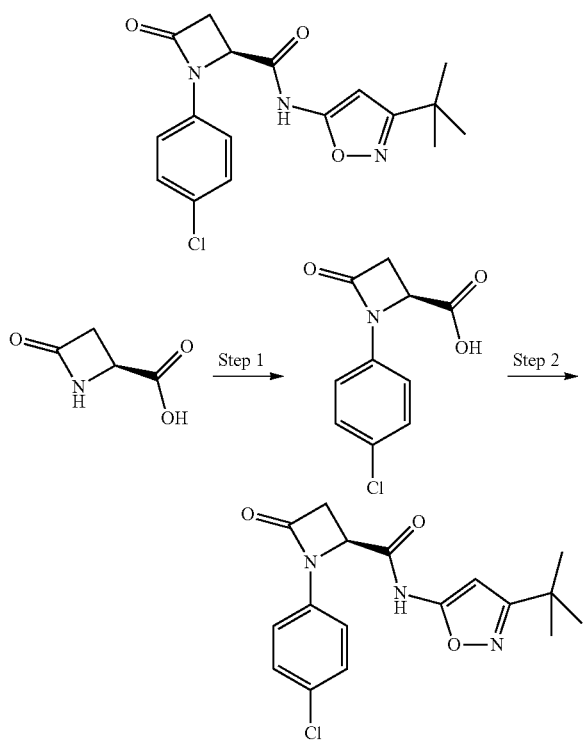

Step 1: Synthesis of (S)-1-(4-Chloro-phenyl)-4-oxo-azetidine-2-carboxylic acid

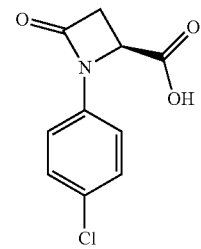

To a stirred suspension of (S)-4-oxo-azetidine-2-carboxylic acid (1.0 g; 8.689 mmol) in 1,2-dichloroethane (35 mL) 1,8-diazabicyclo[5,4,0]undec-7-ene (DBU) (3.1 mL; 20.854 mmol) is added at room temperature. After 10 min di-µ-hydroxy-bis[N,N,N',N'-tetramethylenediamine)-copper (II) chloride (Cu-TMEDA) (1.614 g; 3.476 mmol) is added to the clear solution. The mixture is stirred for 10 min and 4-chlorophenylboronic acid (1.495 g; 9.558 mmol) is added. After 20 hours, solvent is evaporated in vacuo, the concentrate taken up in saturated sodium bicarbonate solution (150 mL) and the aqueous layer is washed with ethyl acetate (3×100 mL). The aqueous layer is treated with 1N hydrochloric acid to pH 2 and extracted with ethyl acetate (3×100 mL). Combined organic extracts washed with brine (2×50 mL), dried over anhydrous sodium sulfate and solvent removed in vacuo to give the title compound as an off-white solid, m/z 226 [M+H⁺]

Step 2: Synthesis of (S)-1-(4-Chloro-phenyl)-4-oxo-azetidine-2-carboxylic acid (3-tert-butyl-isoxazol-5-yl)-amide

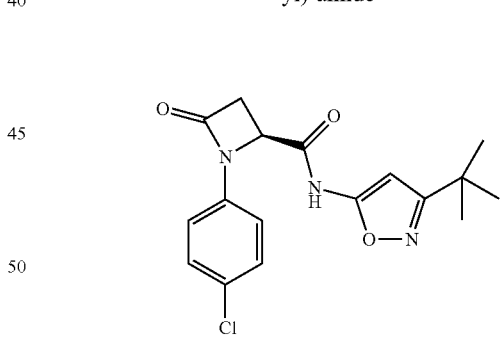

To a cold slurry of (S)-1-(4-Chloro-phenyl)-4-oxo-azetidine-2-carboxylic acid (0.2 g; 1.037 mmol) and 5-amino-3-tert-butylisoxazole (0.145 g; 1.037 mmol) in pyridine (1.258 mL; 15.555 mmol) is added phosphorous oxychloride (0.116 mL; 1.244 mmol). The mixture is stirred at 0° C. for 30 minutes and then diluted with water and extracted with ethyl acetate several times. The organics are combined and washed with water and brine, dried over Na2SO4, filtered and concentrated in vacuo. Purification by preparative HPLC affords title compound, m/z 348 [M+H⁺]

Compounds in Table 6 Method G are prepared in a similar manner.

Method H:

Synthesis of (S)-1-(3-Chloro-5-trifluoromethyl-pyridin-2-yl)-azetidine-2-carboxylic acid [3-(2-hydroxy-1,1-dimethyl-ethyl)-isoxazol-5-yl]-amide
(Example 54)

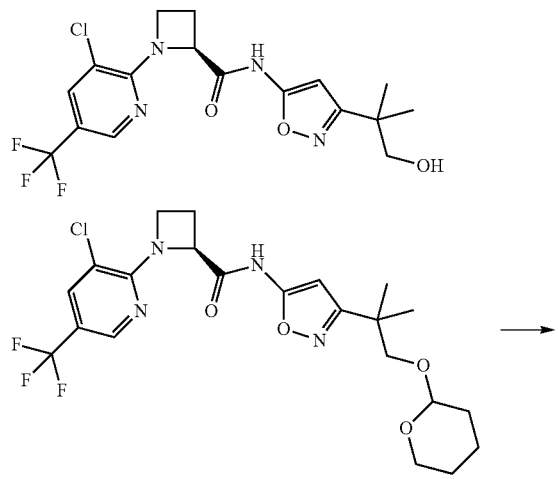

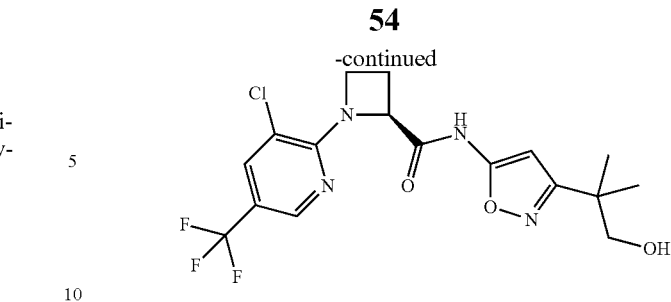

Pyridinium p-toluenesulfonate (13.3 mg; 0.053 mmol) is added to a solution of (S)-1-(3-Chloro-5-trifluoromethyl-pyridin-2-yl)-azetidine-2-carboxylic acid {3-[1,1-dimethyl-2-(tetrahydro-pyran-2-yloxy)-ethyl]-isoxazol-5-yl}-amide (204 mg; 0.406 mmol) in ethanol (2 mL). The reaction mixture is stirred at 55° C. for 5 hours and more pyridinium p-toluenesulfonate (15 mg; 0.060 mmol) is added and the reaction mixture is stirred at 55° C. for 18 hours. After this time, the reaction mixture is concentrated and then diluted with ethyl acetate. It is washed with saturated NaHCO3 aqueous solution. The layers are separated and the aqueous layer is extracted with ethyl acetate once. The organics are combined and washed with brine, dried over Na2SO4, filtered and concentrated in vacuo. Purification by flash chromatography on silica gel using ethyl acetate/hexanes provides the title compound, m/z 419 [M+H$^+$]

Compounds in Table 6 Method H are prepared in a similar manner.

TABLE 6

| Example | Structure | m/z [M + H$^+$] | Method |
|---|---|---|---|
| 1 | 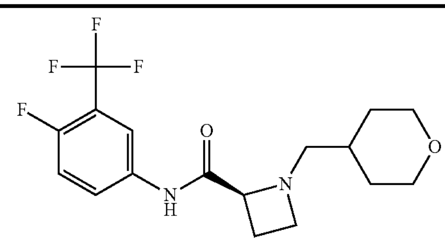 | 361 | C1 |
| 2 | 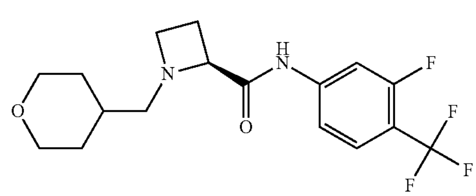 [SMILES: O=C(Nc1ccc(C(F)(F)F)c(F)c1)[C@@H]1CCN1CC1CCOCC1] | 361 | C1 |
| 3 | 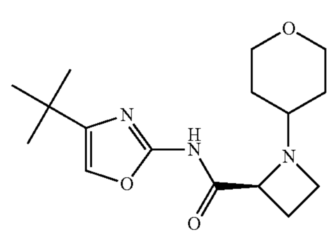 | 308 | C1 |

TABLE 6-continued

| Example | Structure | m/z [M + H⁺] | Method |
|---------|-----------|--------------|--------|
| 4 | 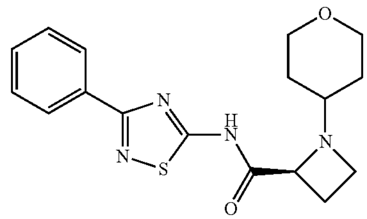 [SMILES: O=C(Nc1nc(-c2ccccc2)ns1)[C@@H]1CCN1C1CCOCC1] | 345 | C1 |
| 5 | 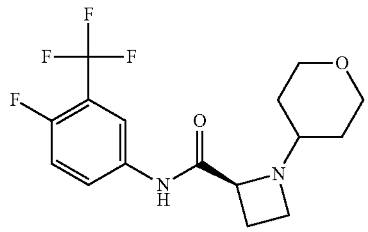 [SMILES: O=C(Nc1ccc(F)c(C(F)(F)F)c1)[C@@H]1CCN1C1CCOCC1] | 347 | C1 |
| 6 | 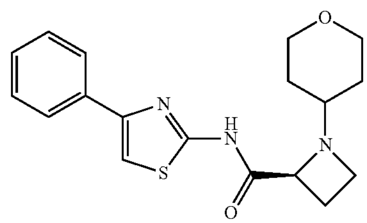 [SMILES: O=C(Nc1nc(-c2ccccc2)cs1)[C@@H]1CCN1C1CCOCC1] | 344 | C1 |
| 7 | 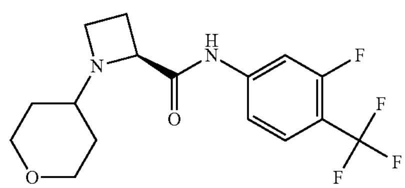 [SMILES: O=C(Nc1ccc(C(F)(F)F)c(F)c1)[C@@H]1CCN1C1CCOCC1] | 347 | C1 |
| 8 | 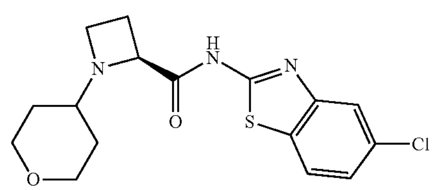 [SMILES: O=C(Nc1nc2cc(Cl)ccc2s1)[C@@H]1CCN1C1CCOCC1] | 352 | C1 |
| 9 | 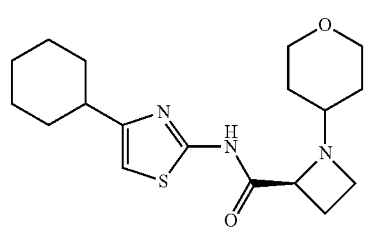 [SMILES: O=C(Nc1nc(C2CCCCC2)cs1)[C@@H]1CCN1C1CCOCC1] | 350 | C1 |
| 10 | 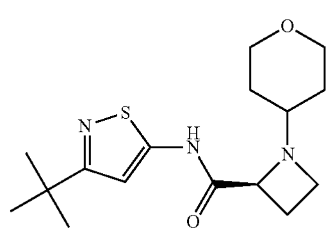 [SMILES: CC(C)(C)c1cc(NC(=O)[C@@H]2CCN2C2CCOCC2)sn1] | 324 | C3 |

TABLE 6-continued

| Example | Structure | m/z [M + H⁺] | Method |
|---------|-----------|--------------|--------|
| 11 | 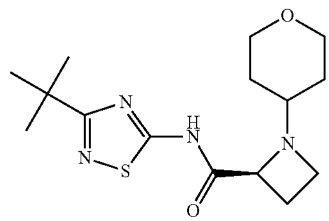 | 325 | C3 |
| 12 | 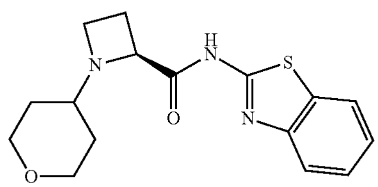 [SMILES: O=C(Nc1nc2ccccc2s1)[C@@H]1CCN1C1CCOCC1] | 318 | C3 |
| 13 | 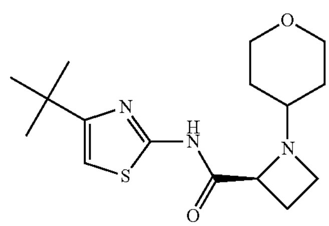 [SMILES: CC(C)(C)c1csc(NC(=O)[C@@H]2CCN2C2CCOCC2)n1] | 324 | C3 |
| 14 | 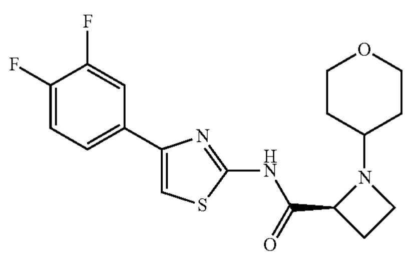 [SMILES: O=C(Nc1nc(-c2ccc(F)c(F)c2)cs1)[C@@H]1CCN1C1CCOCC1] | 380 | C3 |
| 15 | 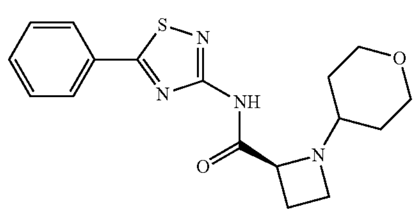 [SMILES: O=C(Nc1nsc(-c2ccccc2)n1)[C@@H]1CCN1C1CCOCC1] | 345 | C3 |
| 16 | 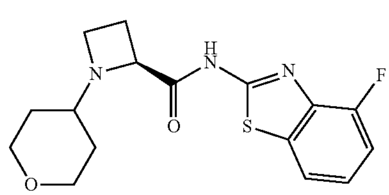 [SMILES: O=C(Nc1nc2c(F)cccc2s1)[C@@H]1CCN1C1CCOCC1] | 336 | C3 |
| 17 | 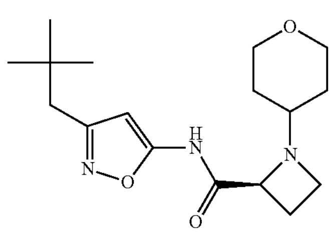 [SMILES: CC(C)(C)Cc1cc(NC(=O)[C@@H]2CCN2C2CCOCC2)on1] | 322 | C3 |

TABLE 6-continued

| Example | Structure | m/z [M + H⁺] | Method |
|---------|-----------|--------------|--------|
| 18 | 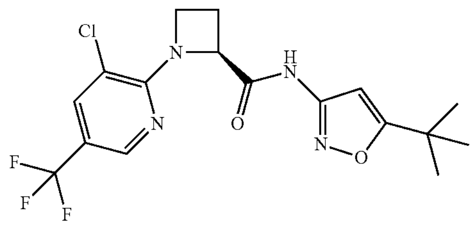 [SMILES: CC(C)(C)c1cc(NC(=O)[C@@H]2CCN2c2ncc(C(F)(F)F)cc2Cl)no1] | 403 | A |
| 19 | 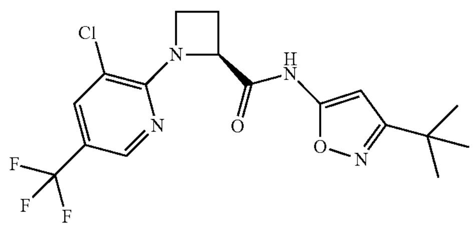 [SMILES: CC(C)(C)c1cc(NC(=O)[C@@H]2CCN2c2ncc(C(F)(F)F)cc2Cl)on1] | 403 | A |
| 20 | 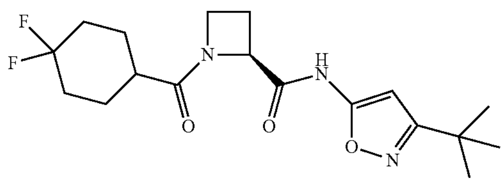 [SMILES: CC(C)(C)c1cc(NC(=O)[C@@H]2CCN2C(=O)C2CCC(F)(F)CC2)on1] | 370 | B |
| 21 | 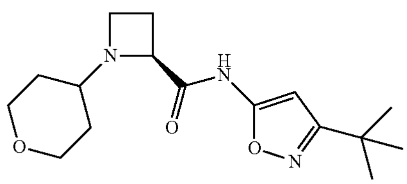 | 308 | C1 |
| 22 | 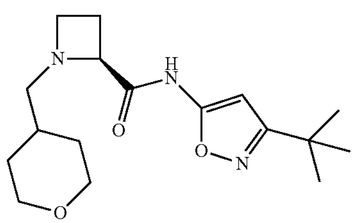 [SMILES: CC(C)(C)c1cc(NC(=O)[C@@H]2CCN2CC2CCOCC2)on1] | 322 | C1 |
| 23 | 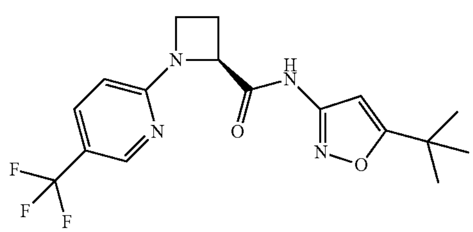 [SMILES: CC(C)(C)c1cc(NC(=O)[C@@H]2CCN2c2ccc(C(F)(F)F)cn2)no1] | 369 | A |
| 24 | 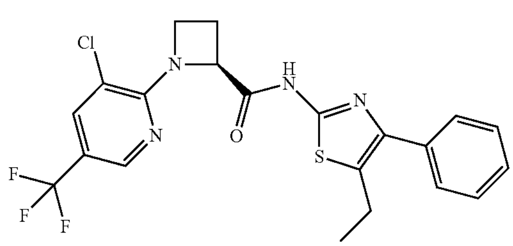 [SMILES: CCc1sc(NC(=O)[C@@H]2CCN2c2ncc(C(F)(F)F)cc2Cl)nc1-c1ccccc1] | 467 | A |

TABLE 6-continued

| Example | Structure | m/z [M + H+] | Method |
|---|---|---|---|
| 25 | 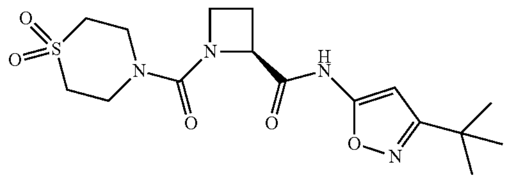 [SMILES: CC(C)(C)c1cc(NC(=O)[C@@H]2CCN2C(=O)N2CCS(=O)(=O)CC2)on1] | 385 | D |
| 26 | 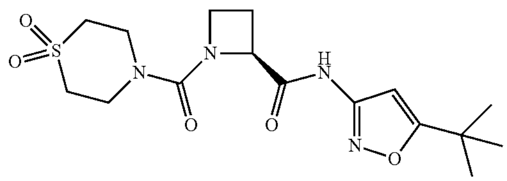 [SMILES: CC(C)(C)c1cc(NC(=O)[C@@H]2CCN2C(=O)N2CCS(=O)(=O)CC2)no1] | 385 | D |
| 27 | 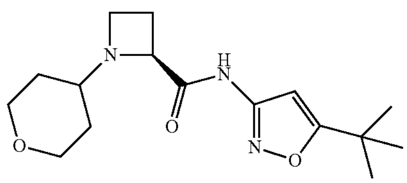 [SMILES: CC(C)(C)c1cc(NC(=O)[C@@H]2CCN2C2CCOCC2)no1] | 308 | C1 |
| 28 | 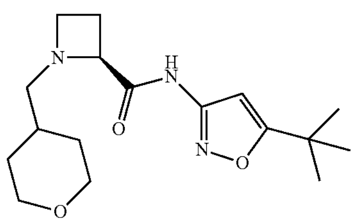 [SMILES: CC(C)(C)c1cc(NC(=O)[C@@H]2CCN2CC2CCOCC2)no1] | 322 | C1 |
| 29 | 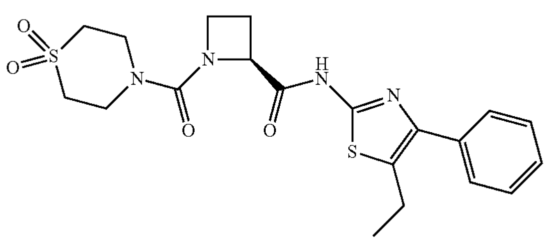 [SMILES: CCc1sc(NC(=O)[C@@H]2CCN2C(=O)N2CCS(=O)(=O)CC2)nc1-c1ccccc1] | 449 | D |
| 30 | 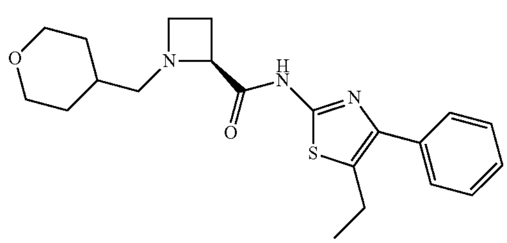 [SMILES: CCc1sc(NC(=O)[C@@H]2CCN2CC2CCOCC2)nc1-c1ccccc1] | 386 | C2 |
| 31 | 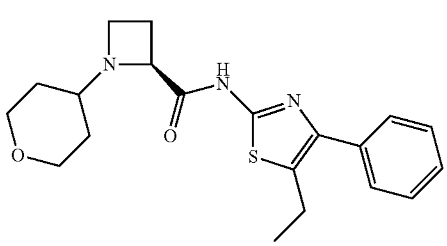 [SMILES: CCc1sc(NC(=O)[C@@H]2CCN2C2CCOCC2)nc1-c1ccccc1] | 372 | C1 |

TABLE 6-continued
| Example | Structure | m/z [M + H+] | Method |
|---------|-----------|--------------|--------|
| 32 | 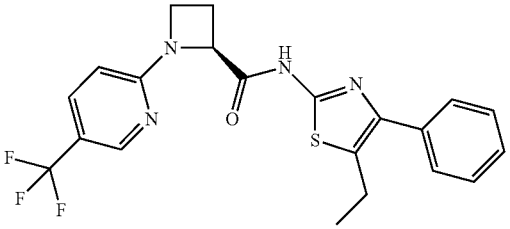 [SMILES: CCc1sc(NC(=O)[C@@H]2CCN2c2ccc(C(F)(F)F)cn2)nc1-c1ccccc1] | 433 | A |
| 33 | 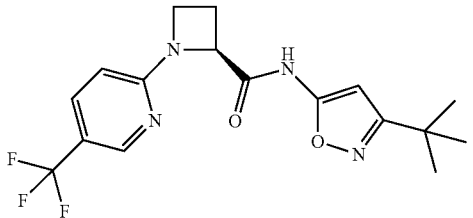 [SMILES: CC(C)(C)c1cc(NC(=O)[C@@H]2CCN2c2ccc(C(F)(F)F)cn2)on1] | 369 | A |
| 34 | 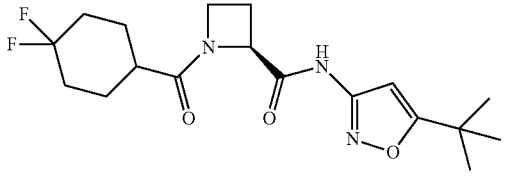 [SMILES: CC(C)(C)c1cc(NC(=O)[C@@H]2CCN2C(=O)C2CCC(F)(F)CC2)no1] | 370 | B |
| 35 | 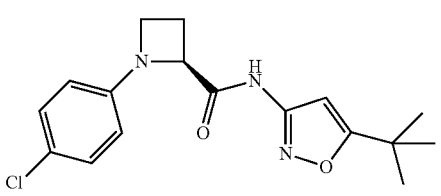 [SMILES: CC(C)(C)c1cc(NC(=O)[C@@H]2CCN2c2ccc(Cl)cc2)no1] | 334 | E |
| 36 | 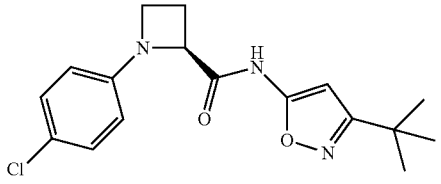 [SMILES: CC(C)(C)c1cc(NC(=O)[C@@H]2CCN2c2ccc(Cl)cc2)on1] | 334 | E |
| 37 | 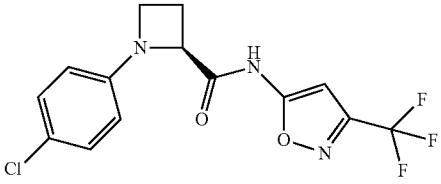 [SMILES: O=C(Nc1cc(C(F)(F)F)no1)[C@@H]1CCN1c1ccc(Cl)cc1] | 346 | E |
| 38 | 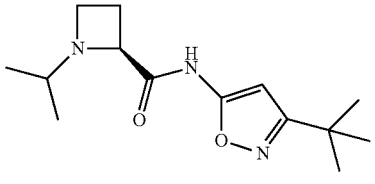 [SMILES: CC(C)N1CC[C@H]1C(=O)Nc1cc(C(C)(C)C)no1] | 266 | C1 |

TABLE 6-continued

| Example | Structure | m/z [M + H⁺] | Method |
|---------|-----------|--------------|--------|
| 39 | 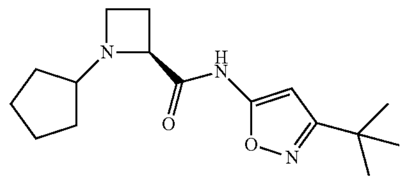 [SMILES: CC(C)(C)c1cc(NC(=O)[C@@H]2CCN2C2CCCC2)on1] | 292 | C1 |
| 40 | 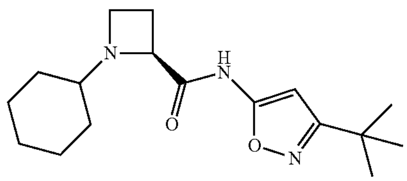 [SMILES: CC(C)(C)c1cc(NC(=O)[C@@H]2CCN2C2CCCCC2)on1] | 306 | C1 |
| 41 | 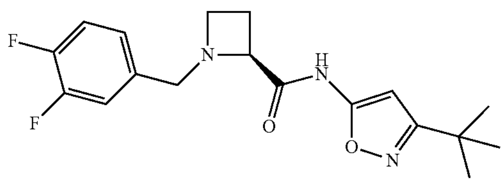 [SMILES: CC(C)(C)c1cc(NC(=O)[C@@H]2CCN2Cc2ccc(F)c(F)c2)on1] | 350 | C1 |
| 42 | 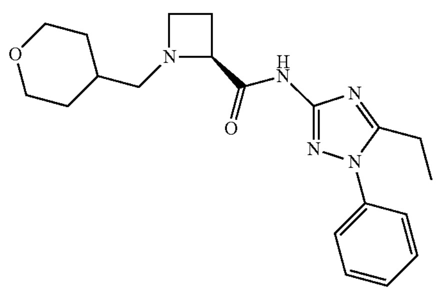 [SMILES: CCc1nc(NC(=O)[C@@H]2CCN2CC2CCOCC2)nn1-c1ccccc1] | 370 | C1 |
| 43 | 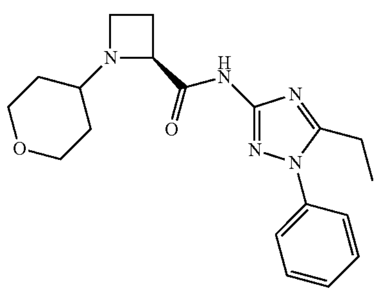 [SMILES: CCc1nc(NC(=O)[C@@H]2CCN2C2CCOCC2)nn1-c1ccccc1] | 356 | C1 |
| 44 | 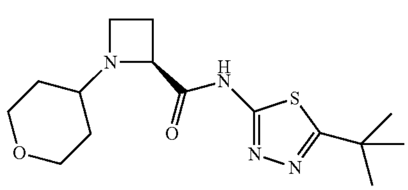 [SMILES: CC(C)(C)c1nnc(NC(=O)[C@@H]2CCN2C2CCOCC2)s1] | 325 | C1 |
| 45 | 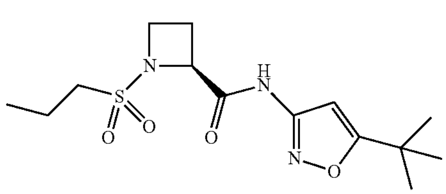 [SMILES: CCCS(=O)(=O)N1CC[C@H]1C(=O)Nc1cc(C(C)(C)C)on1] | 330 | F |

TABLE 6-continued

| Example | Structure | m/z [M + H+] | Method |
|---|---|---|---|
| 46 | 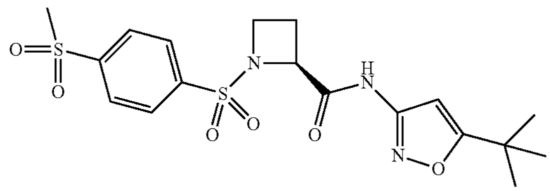 [SMILES: CC(C)(C)c1cc(NC(=O)[C@@H]2CCN2S(=O)(=O)c2ccc(S(C)(=O)=O)cc2)no1] | 442 | F |
| 47 | 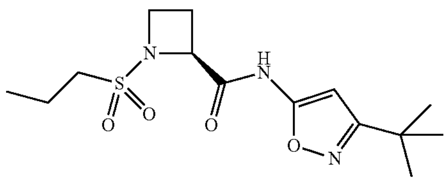 [SMILES: CCCS(=O)(=O)N1CC[C@H]1C(=O)Nc1cc(C(C)(C)C)no1] | 330 | F |
| 48 | 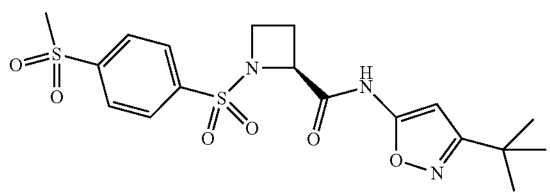 [SMILES: CC(C)(C)c1cc(NC(=O)[C@@H]2CCN2S(=O)(=O)c2ccc(S(C)(=O)=O)cc2)on1] | 442 | F |
| 49 | 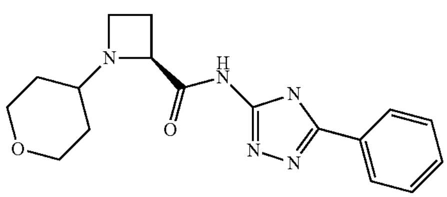 [SMILES: O=C(Nc1nnc(-c2ccccc2)[nH]1)[C@@H]1CCN1C1CCOCC1] | 328 | C1 |
| 50 | 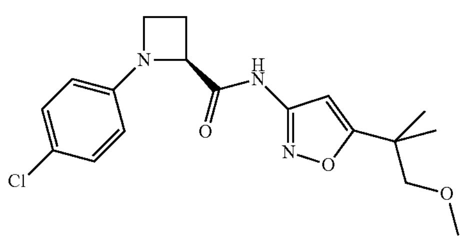 [SMILES: COCC(C)(C)c1cc(NC(=O)[C@@H]2CCN2c2ccc(Cl)cc2)no1] | 364 | E |
| 51 | 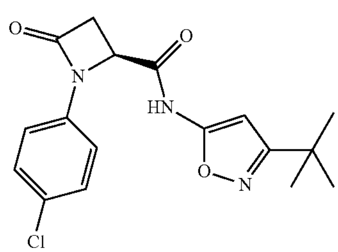 [SMILES: CC(C)(C)c1cc(NC(=O)[C@@H]2CC(=O)N2c2ccc(Cl)cc2)on1] | 348 | G |
| 52 | 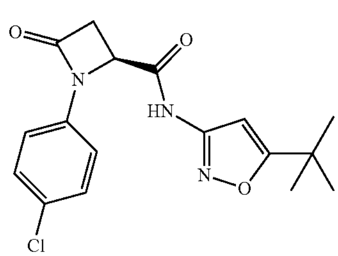 [SMILES: CC(C)(C)c1cc(NC(=O)[C@@H]2CC(=O)N2c2ccc(Cl)cc2)no1] | 348 | G |

TABLE 6-continued
| Example | Structure | m/z [M + H+] | Method |
|---|---|---|---|
| 53 | 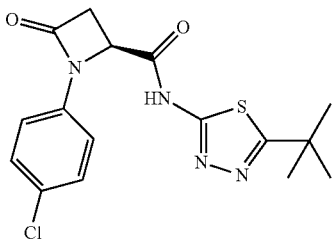 [SMILES: CC(C)(C)c1nnc(NC(=O)[C@@H]2CC(=O)N2c2ccc(Cl)cc2)s1] | 365 | G |
| 54 | 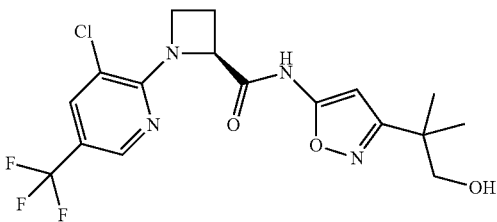 [SMILES: CC(C)(CO)c1cc(NC(=O)[C@@H]2CCN2c2ncc(C(F)(F)F)cc2Cl)on1] | 419 | H |
| 55 | 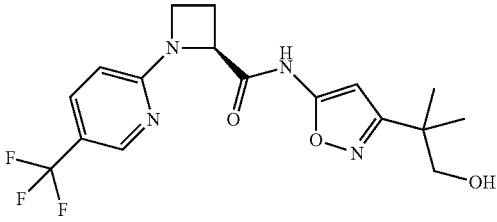 [SMILES: CC(C)(CO)c1cc(NC(=O)[C@@H]2CCN2c2ccc(C(F)(F)F)cn2)on1] | 385 | H |
| 56 | 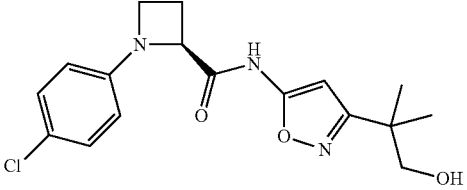 [SMILES: CC(C)(CO)c1cc(NC(=O)[C@@H]2CCN2c2ccc(Cl)cc2)on1] | 350 | H |
| 57 | 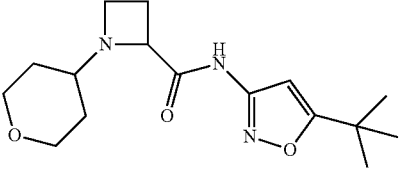 [SMILES: CC(C)(C)c1cc(NC(=O)C2CCN2C2CCOCC2)no1] | 308 | C1 |
| 58 | 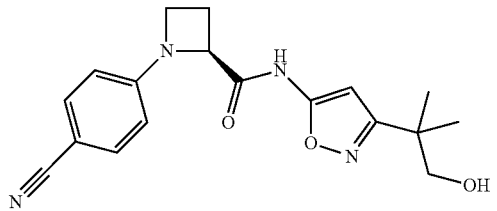 [SMILES: CC(C)(CO)c1cc(NC(=O)[C@@H]2CCN2c2ccc(C#N)cc2)on1] | 341 | H |
| 59 | 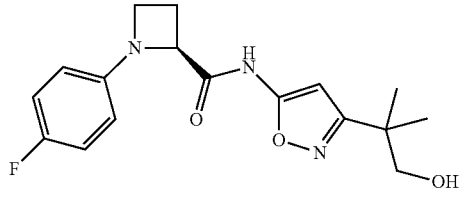 [SMILES: CC(C)(CO)c1cc(NC(=O)[C@@H]2CCN2c2ccc(F)cc2)on1] | 334 | H |

TABLE 6-continued

| Example | Structure | m/z [M + H⁺] | Method |
|---|---|---|---|
| 60 | 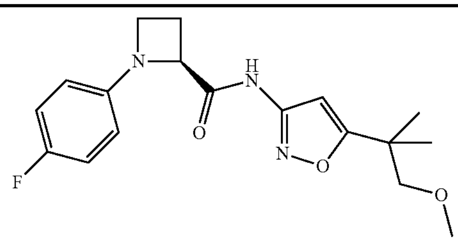 | 348 | E |
| 61 | 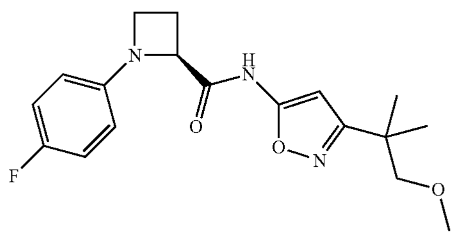 [SMILES: COCC(C)(C)c1cc(NC(=O)[C@@H]2CCN2c2ccc(F)cc2)on1] | 348 | E |
| 62 | 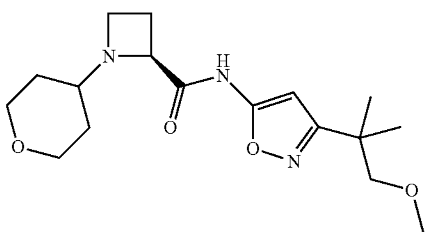 [SMILES: COCC(C)(C)c1cc(NC(=O)[C@@H]2CCN2C2CCOCC2)on1] | 338 | C1 |

Assessment of Biological Properties

The biological properties of the compounds of the invention were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$ M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). IC50 values for each compound were calculated as the concentration of compound that inhibits the specific binding of the radioactively labeled ligand to the receptor by 50% using the XLFit 4.1 four parameter logistic model. IC50 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays compounds were found to exhibit agonistic activity and thus to be particularly well suited for the treatment of pain as well as for the treatment of inflammation. Preferred compounds had EC 50 values<500 nM.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases,;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

The invention claimed is:

1. A compound of the formula (I)

(I)

wherein:
Ar$_1$ is chosen from carbocycle, heterocyclyl and heteroaryl each optionally substituted by 1-3 C$_{1-5}$ alkyl which is optionally substituted with halogens, C$_{1-5}$ alkoxy, hydroxyl, CN, halogen, NO$_2$, —S(O)$_m$—C$_{1-5}$ alkyl, —CO$_2$—C$_{1-5}$ alkyl, —NH(C$_{1-5}$ alkyl)—CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl, carbocycle or heterocyclyl;
Ar$_2$ is chosen from carbocycle, heterocyclyl and heteroaryl each optionally substituted by 1-3 C$_{1-10}$ alkyl which is optionally substituted with halogens, C$_{3-10}$ cycloalkyl, carbocycle, C$_{1-10}$ alkylcarbocycle, heteroaryl, CN or halogen, wherein the C$_{1-10}$ alkyl and carbocycle may be additionally optionally substituted by halogen, hydroxyl or C$_{1-5}$ alkoxy;
with the proviso that Ar$_1$ and Ar$_2$ cannot simultaneously be unsubstituted phenyl;
L$_1$ is a bond;
L$_2$ is a bond;
R$_1$ is chosen from hydrogen, oxo (═O) and OH;
m is 0, 1 or 2;
or a pharmaceutically acceptable salt thereof.

2. The compound according to claim 1 and wherein:
Ar$_1$ is chosen from phenyl, C$_{3-6}$ cycloalkyl, dioxanyl, tetrahydrofuranyl, tetrahydropyranyl, thiomorpholinyl, 1,1-Dioxo-1λ$^6$-thiomorpholinyl, morpholinyl and pyridinyl, each optionally substituted by 1-3 C$_{1-5}$ alkyl which is optionally substituted with halogens, C$_{1-5}$ alkoxy, hydroxyl, CN, S(O)$_m$—C$_{1-3}$ alkyl or halogen;
Ar$_2$ is chosen from oxazolyl, isoxazolyl, oxadiazoyl, thiazoyl, thiadiazoyl, benzothiazoyl, triazoyl, isothiazoyl, phenyl, pyrimidinyl, pyridizinyl, pyrazinyl and pyridinyl, each optionally substituted by 1-3 C$_{1-6}$ alkyl which is optionally substituted with halogens, C$_{1-5}$ alkoxyl, or hydroxyl, phenyl optionally substituted with halogens, halogen or C$_{3-8}$ cycloalkyl;
R$_1$ is hydrogen;
L$_1$ is a bond;
L$_2$ is a bond.

3. The compound according to claim 2 and wherein:
Ar$_1$ is chosen from phenyl, C$_{3-6}$ cycloalkyl, tetrahydropyranyl and pyridinyl, each optionally substituted by 1-3 C$_{1-5}$ alkyl, trifluoromethyl, S(O)$_m$—C$_{1-3}$ alkyl or halogen;
Ar$_2$ is chosen from isoxazolyl, oxazolyl, thiazolyl, phenyl, benzothiazolyl, isothiazolyl and thiadiazolyl, each optionally substituted by 1-3 C$_{1-5}$ alkyl optionally substituted with C$_{1-5}$ alkoxyl, or hydroxyl, phenyl optionally substituted with halogen, halogen, C$_{3-6}$ cycloalkyl or trifluoromethyl;
L$_1$ is a bond.

4. The compound according to claim 3 and wherein:
Ar$_1$ is chosen from phenyl, cyclopentyl, cyclohexyl, tetrahydropyranyl and pyridinyl, each optionally substituted by 1-3 C$_{1-3}$ alkyl, trifluoromethyl, methylsulfonyl or halogen.

5. The compound according to claim 4 and wherein:
Ar$_2$ is chosen from

6. The compound according claim 5 and wherein:
Ar$_2$ is chosen from

7. A compound of the formula (II)

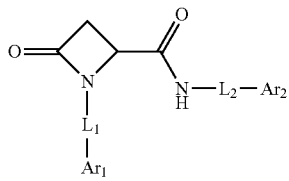

wherein

Ar₁ is chosen from phenyl, $C_{3-6}$ cycloalkyl, dioxanyl, tetrahydrofuranyl, tetrahydropyranyl, oxazolyl, isoxazolyl, oxadiazoyl, thiazoyl, thiadiazoyl, benzothiazoyl, triazoyl, isothiazoyl, pyridinyl, pyrimidinyl, pyrazinyl, pyridazinyl, pyrrolyl, imidazolyl and pyrazolyl each optionally substituted by 1-3 $C_{1-6}$ alkyl which is optionally substituted with halogens, $S(O)_m$—$C_{1-3}$ alkyl, $C_{1-6}$ alkoxy, hydroxyl or halogen;

Ar₂ is chosen from oxazolyl, isoxazolyl, oxadiazoyl, thiazoyl, thiadiazoyl, benzothiazoyl, triazoyl, isothiazoyl, phenyl, pyrimidinyl, pyridizinyl, pyrazinyl and pyridinyl, each optionally substituted by 1-3 $C_{1-6}$ alkyl which is optionally substituted with halogens, $C_{1-6}$ alkoxyl or hydroxyl, phenyl optionally substituted with halogens, halogen, $C_{1-6}$ alkoxyl, or $C_{3-8}$ cycloalkyl;

L₁ is a bond;

L₂ is a bond;

or a pharmaceutically acceptable salt thereof.

8. The compound according to claim 7 and wherein:

Ar₁ is chosen from phenyl, $C_{3-6}$ cycloalkyl, tetrahydropyranyl and pyridinyl, each optionally substituted by 1-3 $C_{1-6}$ alkyl, trifluoromethyl, $S(O)_m$—$C_{1-3}$ alkyl or halogen;

Ar₂ is chosen from isoxazolyl, oxazolyl, thiazolyl, phenyl, benzothiazolyl, isothiazolyl and thiadiazolyl, each optionally substituted by 1-3 $C_{1-6}$ alkyl optionally substituted with $C_{1-6}$ alkoxyl or hydroxyl, phenyl optionally substituted with halogen, halogen, $C_{1-6}$ alkoxyl, $C_{3-6}$ cycloalkyl or trifluoromethyl;

L₁ is a bond.

9. The compound according to claim 8 and wherein:

Ar₁ is chosen from phenyl, cyclopentyl, cyclohexyl, tetrahydropyranyl and pyridinyl, each optionally substituted by 1-3 $C_{1-3}$ alkyl, trifluoromethyl or halogen.

10. The compound according to claim 9 and wherein:

Ar₂ is chosen from

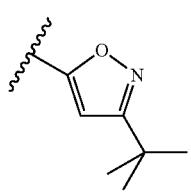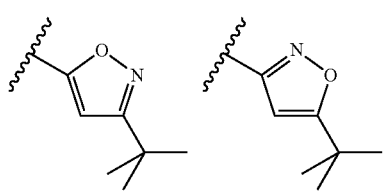

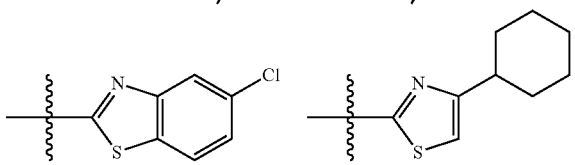

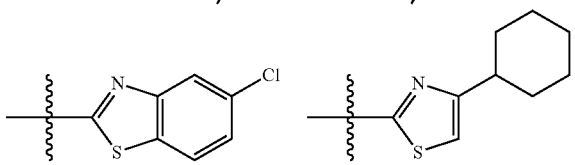

-continued

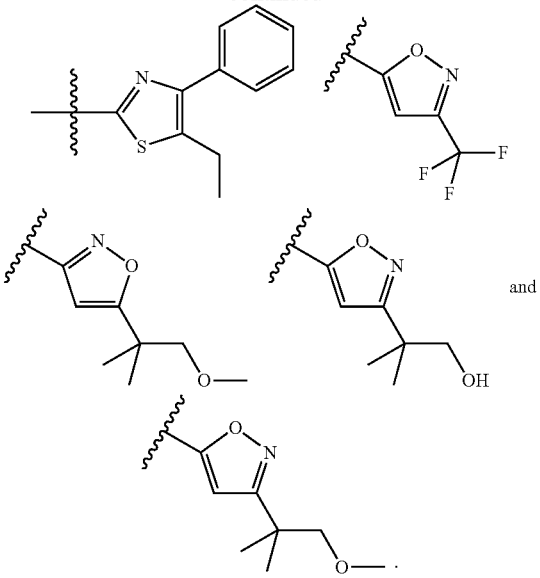

11. The compound according to claim 10 and wherein:

Ar₂ is chosen from

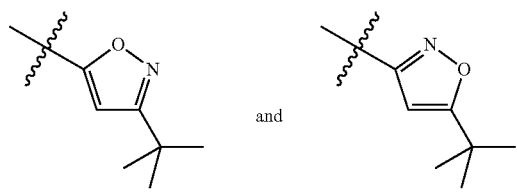

12. A compound of the formula (III)

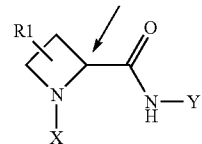

wherein

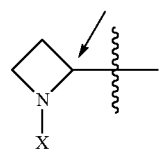

of the formula (III) is chosen from A1-A15 of Table I, and

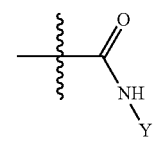

of the formula (III) is chosen from B1-B25 of Table I,

TABLE I
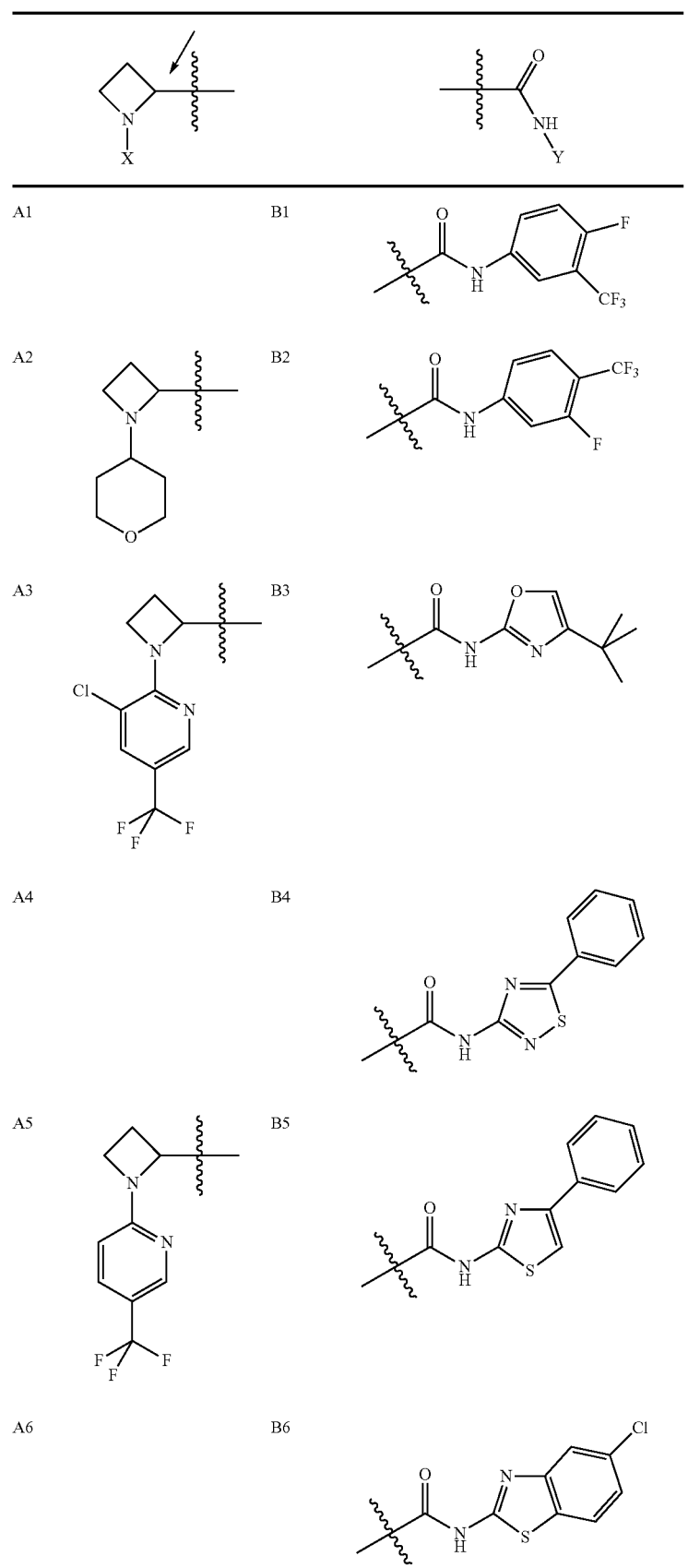

TABLE I-continued
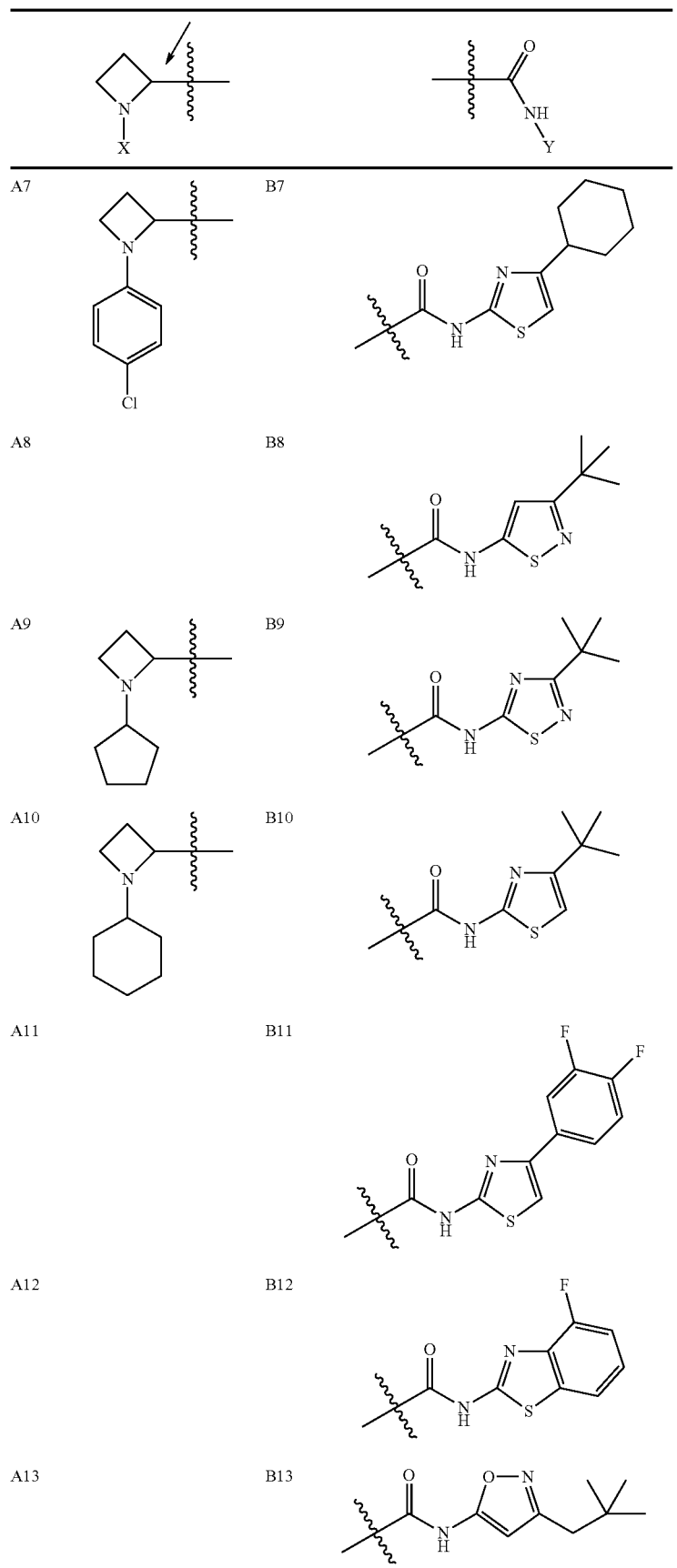

TABLE I-continued
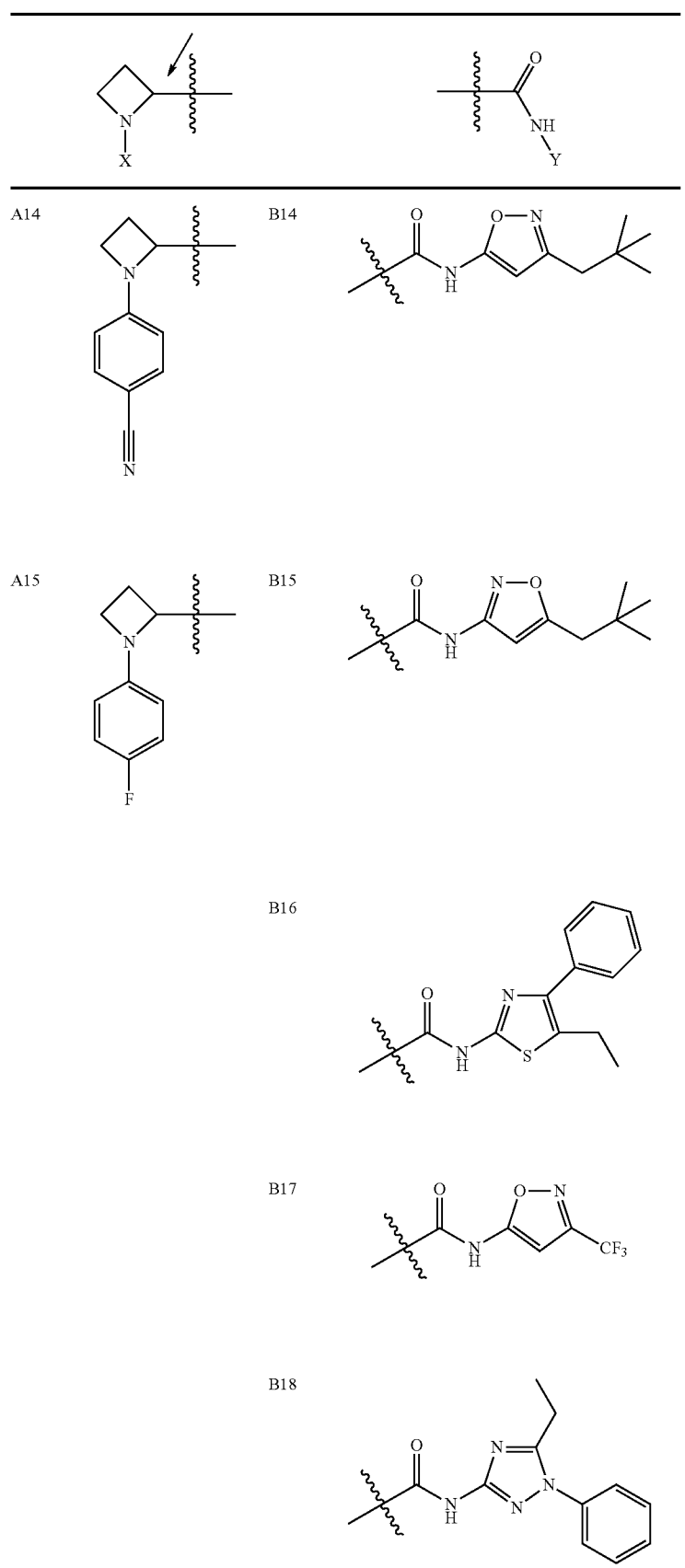

TABLE I-continued
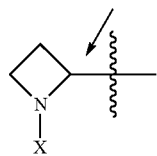 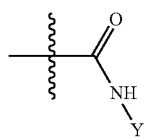
| B19 | 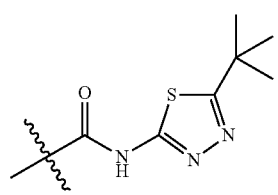 [SMILES: *C(=O)Nc1nnc(C(C)(C)C)s1] |
| B20 | 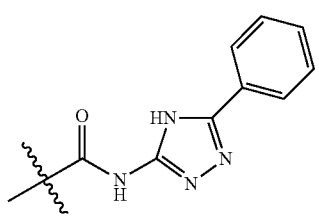 [SMILES: *C(=O)Nc1nnc(-c2ccccc2)[nH]1] |
| B21 | 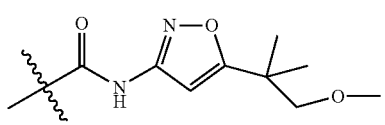 [SMILES: *C(=O)Nc1cc(C(C)(C)COC)on1] |
| B22 | 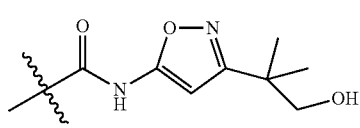 [SMILES: *C(=O)Nc1cc(C(C)(C)CO)no1] |
| B23 | 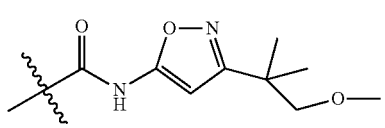 [SMILES: *C(=O)Nc1cc(C(C)(C)COC)no1] |
| B24 | 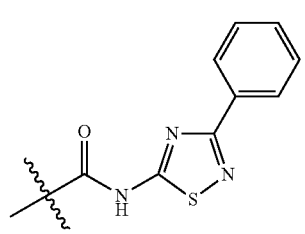 [SMILES: *C(=O)Nc1nc(-c2ccccc2)ns1] |

TABLE I-continued
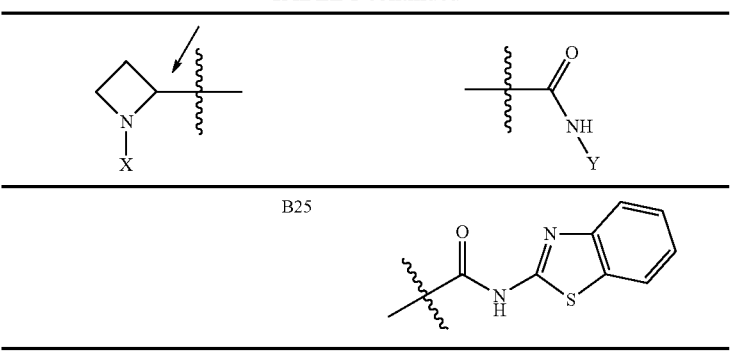
or a pharmaceutically acceptable salt thereof.
13. The compound according to claim 12 wherein the stereogenic carbon in the formula (III) indicated with an arrow is in the (S) configuration.
14. A compound chosen from:
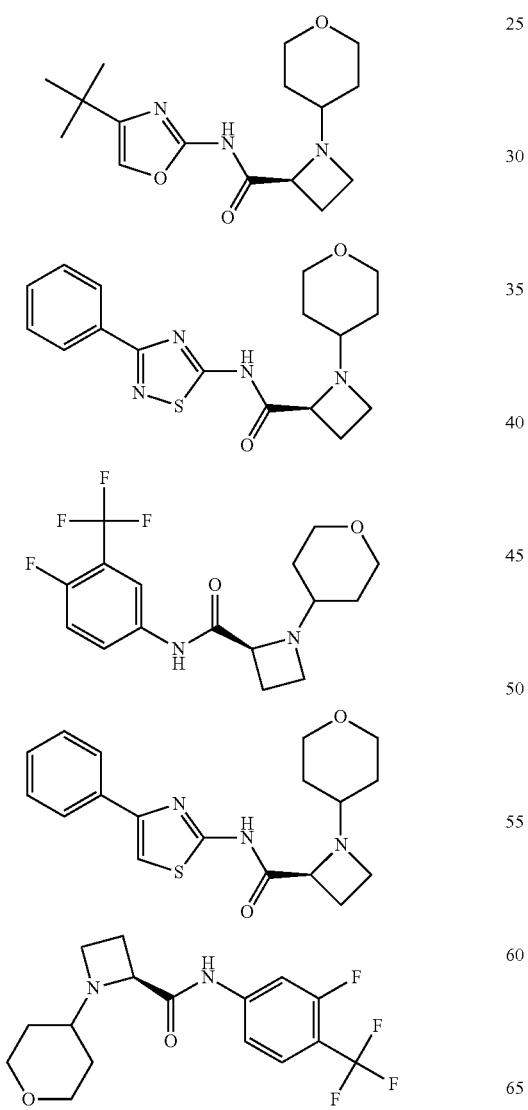
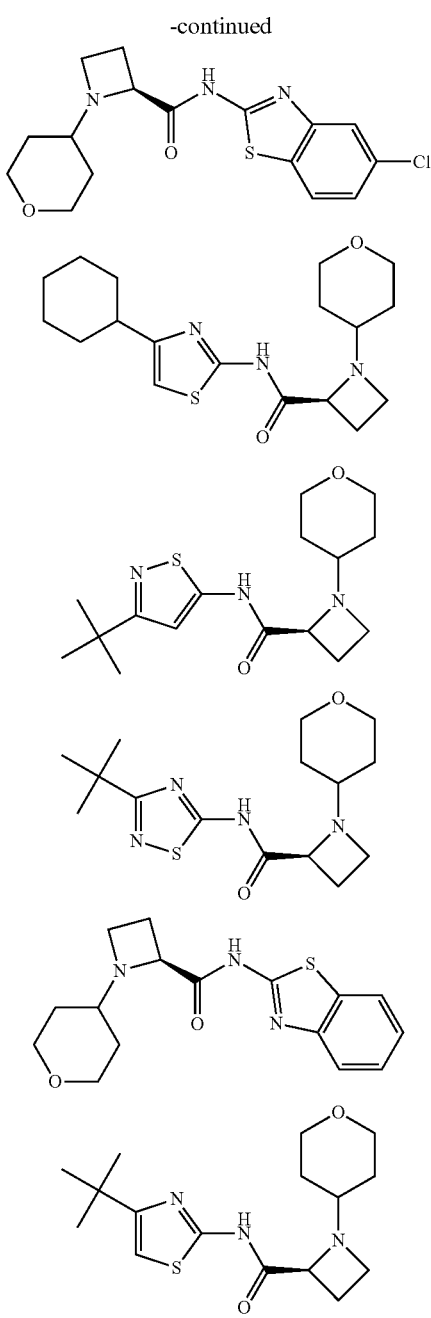

91
-continued
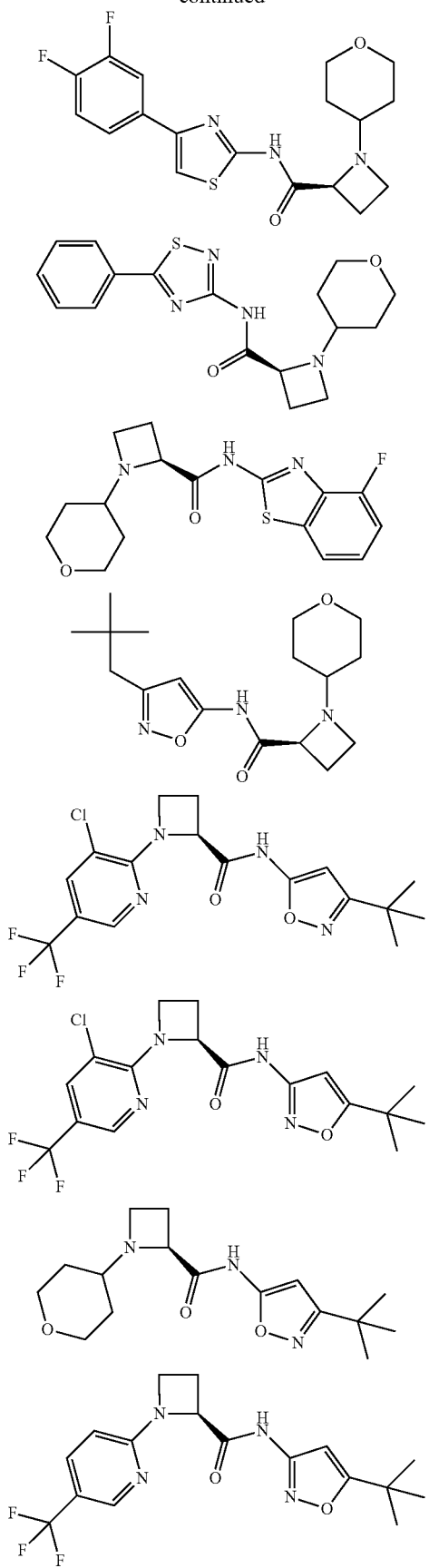
92
-continued
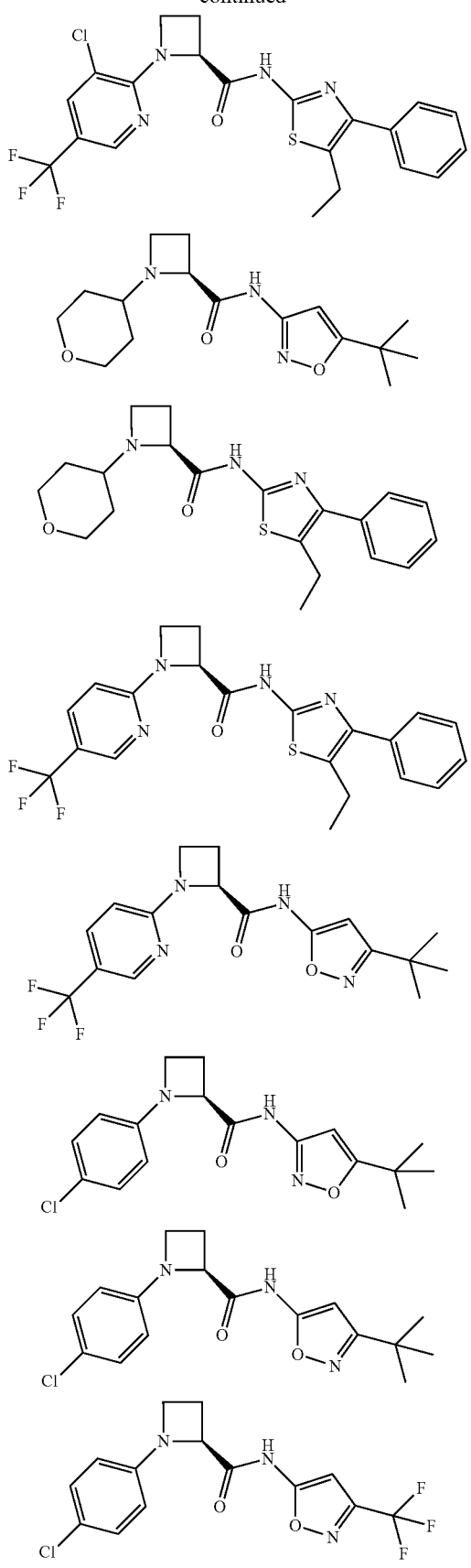

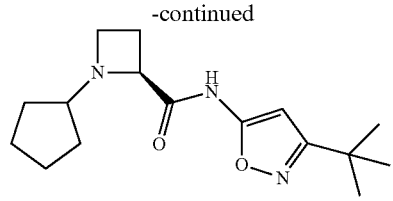
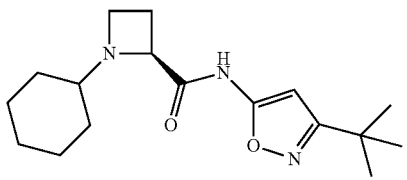
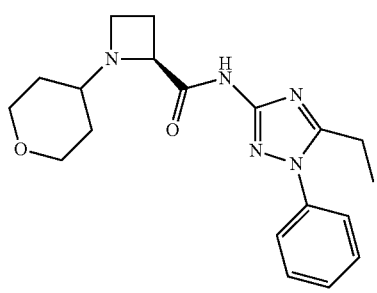
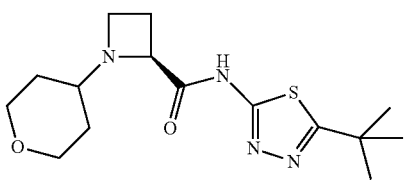
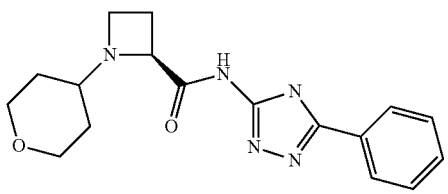
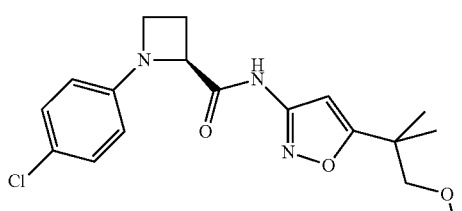
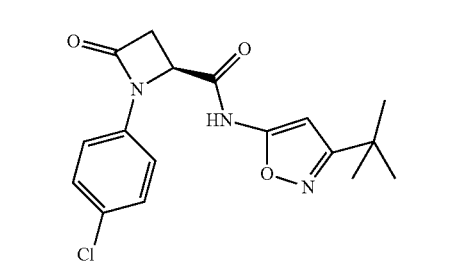
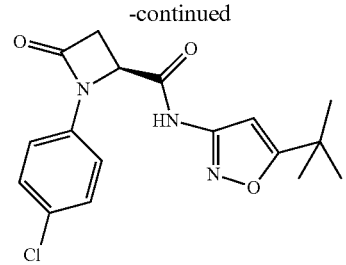
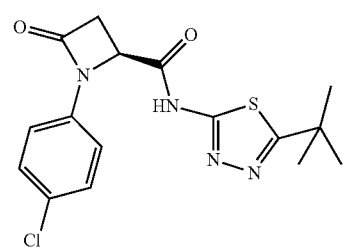
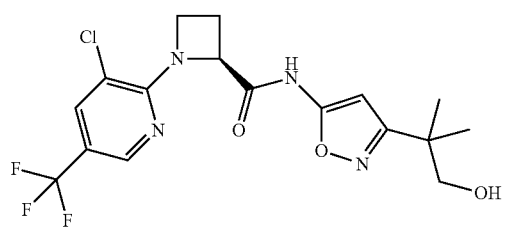
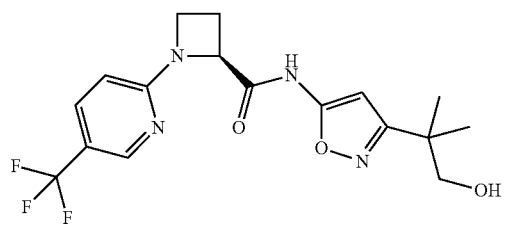
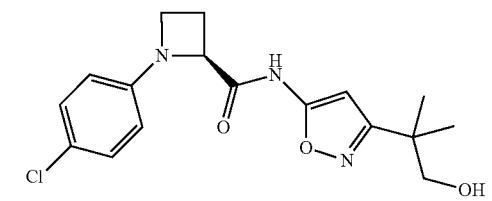
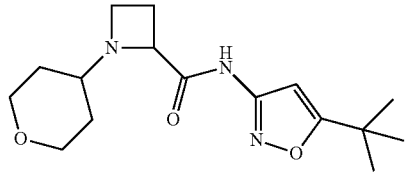
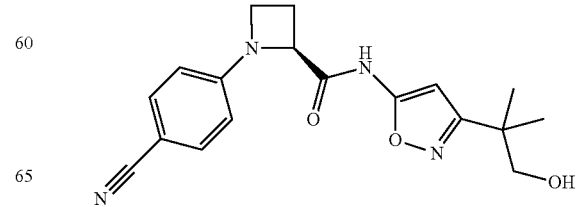

-continued

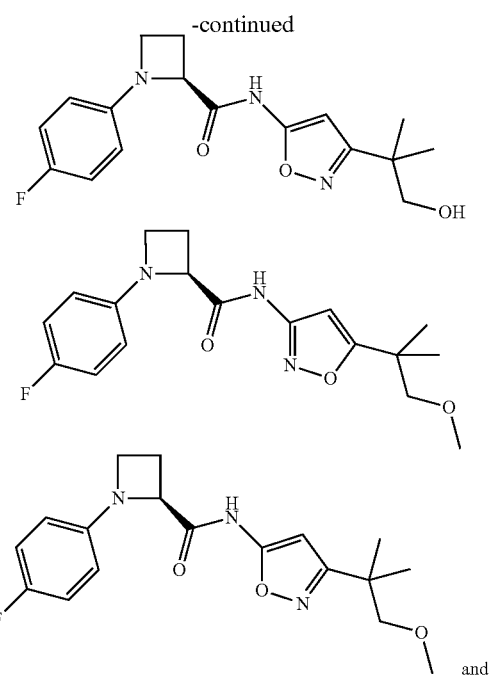

and

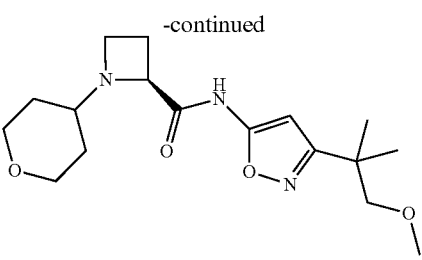

or a pharmaceutically acceptable salt thereof.

15. A pharmaceutical composition comprising a therapeutically effective amount of a compound according to claim 1, 7 or 12 and one or more pharmaceutically acceptable carriers and/or adjuvants.

16. A method of treating pain comprising administering a therapeutically effective amount of a compound according to claim 1, 7 or 12.

17. A method of treating pain wherein the pain is chosen from acute pain, visceral pain, comprising administering a therapeutically effective amount of a compound according to claim 1, 7 or 12.

* * * * *